United States Patent
Reitz et al.

(10) Patent No.: US 10,357,497 B2
(45) Date of Patent: *Jul. 23, 2019

(54) PRO-DRUGS OF RILUZOLE AND THEIR METHOD OF USE FOR THE TREATMENT OF AMYOTROPHIC LATERAL SCLEROSIS

(71) Applicant: Biohaven Pharmaceutical Holding Company Limited, New Haven, CT (US)

(72) Inventors: Allen B. Reitz, Lansdale, PA (US); Garry R. Smith, Royersford, PA (US)

(73) Assignee: Biohaven Pharmaceutical Holding Company Limited, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/410,647

(22) PCT Filed: Jun. 24, 2013

(86) PCT No.: PCT/US2013/047315
§ 371 (c)(1),
(2) Date: Dec. 23, 2014

(87) PCT Pub. No.: WO2013/192610
PCT Pub. Date: Dec. 27, 2013

(65) Prior Publication Data
US 2015/0148329 A1    May 28, 2015

Related U.S. Application Data

(60) Provisional application No. 61/663,573, filed on Jun. 23, 2012.

(51) Int. Cl.
| | | |
|---|---|---|
| *A61K 31/541* | (2006.01) | |
| *A61K 31/428* | (2006.01) | |
| *A61K 31/4439* | (2006.01) | |
| *A61K 31/454* | (2006.01) | |
| *A61K 31/4725* | (2006.01) | |
| *A61K 31/496* | (2006.01) | |
| *A61K 31/5377* | (2006.01) | |

(52) U.S. Cl.
CPC .......... *A61K 31/541* (2013.01); *A61K 31/428* (2013.01); *A61K 31/4439* (2013.01); *A61K 31/454* (2013.01); *A61K 31/4725* (2013.01); *A61K 31/496* (2013.01); *A61K 31/5377* (2013.01)

(58) Field of Classification Search
CPC .............. A61K 31/428; A61K 31/4439; A61K 31/454; A61K 31/4725; A61K 31/496; A61K 31/5377; A61K 31/541
See application file for complete search history.

(56) References Cited

U.S. PATENT DOCUMENTS 5,527,814 A * 6/1996 Louvel ................. A61K 31/425
514/367

FOREIGN PATENT DOCUMENTS

| WO | WO 2009019534 A2 * | 2/2009 | .......... C07C 309/15 |
| WO | WO 2010102923 A2 * | 9/2010 | .......... A61K 9/0095 |
| WO | WO-2013138753 A1 * | 9/2013 | .......... C07D 417/12 |

OTHER PUBLICATIONS

Akamatsu et. al., Anticancer Research, 2009, Potamitis Press, vol. 29, pp. 2195-2204.*
Kuzma-Kozakiewicz et. al., Expert Opinion on Therapeutic Targets, publ. online Dec. 7, 2010; Taylor & Francis, vol. 15(2), pp. 127-143.*
Yacoubian et. al., Biochimica et Biophysica Acta, 2009, Elsevier,vol. 1792, pp. 676-687.*
Weiner, Annals of Neurology, 2009, American Neurological Association, vol. 65, pp. 239-248.*
Haddad et. al., Muscle Nerve, 2003, Wiley Periodicals, vol. 28, pp. 432-437 (Year: 2003).*
Wood, Nature Reviews Neurology, 2015, Nature Publishing Group, vol. 11, p. 547 (Year: 2015).*
Zarate, Expert Opin Drug Metab Toxicol., 2008, NIH, vol. 4(9), pp. 1-17 (Year: 2008).*
Fehlings et. al., The Spine Journal, 2017, vol. 17, Abstract, p. S88 (Year: 2017).*

* cited by examiner

*Primary Examiner* — Sarah Pihonak
(74) *Attorney, Agent, or Firm* — Locke Lord LLP; Ralph A. Loren; Nicholas J. DiCeglie, Jr.

(57) ABSTRACT

Pharmaceutical compositions of the invention include substituted riluzole pro drugs useful for the treatment of amyotrophic lateral sclerosis (ALS) and related disorders through the release of riluzole, especially to avoid patient to patient variability in first pass, hepatic metabolism promoted by Cyp 1A2. Pro-drugs of riluzole have enhanced stability to hepatic metabolism and are delivered into systemic circulation by oral administration, and then cleaved to release riluzole in the plasma via either an enzymatic or general biophysical release process. The invention further includes pro-drugs of riluzole useful for the treatment of disease states that can be treated with riluzole through the release of riluzole from a pro-drug agent.

4 Claims, No Drawings

PRO-DRUGS OF RILUZOLE AND THEIR METHOD OF USE FOR THE TREATMENT OF AMYOTROPHIC LATERAL SCLEROSIS

CROSS-REFERENCE TO RELATED APPLICATIONS

This application claims the benefit of U.S. Provisional Application No. 61/663,573 filed Jun. 23, 2012, which is herein incorporated by reference in its entirety.

STATEMENT OF FEDERALLY FUNDED RESEARCH

This invention was made with government support under grant numbers R43 CA156781 and R44 CA156781 awarded by the National Institutes of Health. The government has certain rights in this invention.

FIELD OF INVENTION

The present invention describes compounds and methods useful as pro-drug agents, useful for the treatment of amyotrophic lateral sclerosis through the release of riluzole. The present invention further relates to compounds and methods useful as pro-drug agents, useful for the treatment of disease states that can be treated with riluzole through the release of riluzole from a pro-drug agent.

BACKGROUND OF THE INVENTION

Amyotrophic lateral sclerosis (ALS) is a debilitating neurological disorder associated with diminished motor function resulting in muscle wasting and death in 3-5 years, often as the result of respiratory failure. ALS is thought to be caused by a combination of both environmental and genetic risk factors, with ca. 15% of the disease prevalence clearly associated with inherited mutations (familial ALS, fALS) such as those associated with superoxide dismutase (SOD1) and on chromosome 9 (GGGGCC repeats). ALS imparts a great deal of suffering upon both patients and caregivers, and places a large burden upon the health care system in that as many as 10 health care professionals are required to provide patient care during the course of the disease. It is estimated that the lifetime risk of developing ALS is 1:1000, and that 15-20 new patients are diagnosed with the disease every day in the U.S. ALS is an orphan indication consisting at any time of 30,000-40,000 individuals in the U.S. and >300,000 worldwide. The financial burden for the treatment of ALS ranges from ca. $3,100 to $5,800 per year, with late stage ventilation treatment costing from ca. $160,000 for in-home to $430,000 per year for institutional treatment. The mean time spent on ventilation in the terminal stage of the disease is three years rendering this a cost-prohibitive option not available to many patients. The only approved treatment for ALS is Rilutek® (riluzole, 1) which increases lifespan by only 2-3 months after 1.5 years of treatment, and is effective at delaying tracheostomy upon bulbar patients. There is a clear unmet medical need for improved treatment options for patients who suffer from ALS.

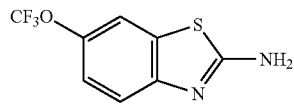

Riluzole (Rilutek®) the only FDA-approved treatment for amyotrophic lateral sclerosis (ALS or Lou Gehrig's disease). Riluzole has a mild side-effect profile among ALS patients. However, the therapeutic utility of riluzole itself in ALS is constrained by rapid first-pass metabolism in the liver and an exceptionally high level of patient-to-patient variability in the extent of the Cyp1A2-mediated oxidative metabolism that is observed. Pro-drugs of riluzole that avoid first pass, hepatic metabolism and are cleaved in plasma to deliver riluzole will provide more predictable pharmacokinetic properties and metabolic profiles for the parent compound, leading to an improved therapeutic effect.

Riluzole is also clinically relevant in additional disease states. These include, but are not limited to, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, and Huntington's disease. Pro-drugs of riluzole will provide more predictable pharmacokinetic properties and metabolic profiles for the parent compound, leading to an improved therapeutic effect in each of the aforementioned disease states.

There is a long felt need for new treatments for ALS that are both disease-modifying and effective in treating ALS patients. The present invention addresses the need to identify new treatments for ALS by indentifying novel pro-drugs of riluzole which possess enhanced stability to hepatic metabolism and are delivered into systemic circulation by oral administration. The riluzole pro-drugs are cleaved to release riluzole in the plasma via either an enzymatic or general biophysical release process.

There is also a long felt need for new treatments for disease states in which riluzole is clinically relevant including, but are not limited to, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, and Huntington's disease. The present invention addresses the need to identify treatments for disease states in which riluzole is clinically relevant by indentifying novel pro-drugs of riluzole which possess enhanced stability to hepatic metabolism and are delivered into systemic circulation by oral administration. The riluzole pro-drugs are cleaved to release riluzole in the plasma via either an enzymatic or general biophysical release process.

BRIEF SUMMARY OF THE INVENTION

The present invention is directed toward riluzole derivatives of formula (I),

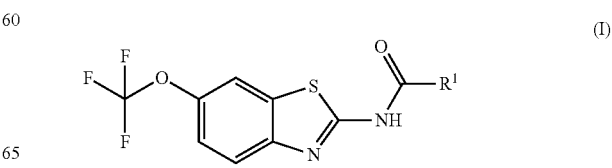

including hydrates, solvates, pharmaceutically acceptable salts, and complexes thereof, wherein:

$R^1$ is selected from the group consisting of $OR^2$, $CR^{3a}R^{3b}NH_2$, $CR^{3a}R^{3b}NR^{7a}R^{7b}$, $CH_2CH_2CO_2R^4$, $CH_2CH_2CONHR^5$, $(CR^{6a}R^{6b})_mNR^{7a}R^{7b}$, $CH_2Ar$, and optionally substituted phenyl ring;

$R^2$ is selected from the group consisting of optionally substituted C1-C6 alkyl and $CH_2(CH_2)_nNR^{8a}R^{8b}$;

n=1 or 2;

$R^{3a}$ and $R^{3b}$ are each independently selected from the group consisting of hydrogen, optionally substituted C1-C6 alkyl, optionally substituted C1-C6 alkenyl, optionally substituted C1-C6 alkynyl, $CH_2R^{4a}$, optionally substituted phenyl, optionally substituted benzyl, optionally substituted $CH_2CH_2Ar$, optionally substituted $CH_2$heteroaryl, $CH_2OR^9$, $CH(CH_3)OR^9$, $CH_2SR^9$, $CH_2CH_2SCH_3$, $CH_2CH_2SO_2CH_3$, $CH_2CH_2CH_2NR^{10a}R^{10b}$, $CH_2COR^{5a}$, and $CH_2CH_2COR^{9a}$;

$R^{3a}$ and $R^{3b}$ are taken together with the atom to which they are bound to form an optionally substituted three to six membered saturated heterocyclic ring comprising two to five carbon atoms and a member selected from the group consisting of O, $NR^{7a}$, S, and $SO_2$;

$R^4$ is selected from the group consisting of hydrogen and optionally substituted C1-C6 Alkyl;

$R^{4a}$ is selected from the group consisting of hydrogen, optionally substituted C1-C6 Alkyl, optionally substituted C3-C6 cycloalkyl, and optionally substituted four to six membered saturated heterocyclic rings comprising three to five carbon atoms and a member selected from the group consisting of O, $NR^{7a}$, S, and $SO_2$;

$R^5$ is selected from the group consisting of hydrogen, optionally substituted C1-C6 Alkyl, $CH_2CH_2NR^{10a}R^{10b}$, and $CH_2R^{11}$;

$R^{6a}$ and $R^{6b}$ are, at each occurrence, independently selected from the group consisting of hydrogen and optionally substituted C1-C6 alkyl;

$R^{6a}$ and $R^{6b}$ are taken together with the atom to which they are bound to form an optionally substituted 6 membered ring;

m=3 or 4;

m=1 or 2;

$R^{7a}$ and $R^{7b}$ are each independently selected from the group consisting of hydrogen, methyl, $COR^{12}$, and $CO2R^{12}$;

$R^{3a}$ and $R^{7a}$ are taken together with the atoms to which they are bound to form an optionally substituted three to six membered ring consisting of all carbons and one nitrogen atom;

$R^{3a}$ and $R^{7a}$ are taken together with the atoms to which they are bound to form an optionally substituted 1,2,3,4-tetrahydro-isoquinoline ring system;

$R^{3a}$ and $R^{7a}$ are taken together with the atoms to which they are bound to form an optionally substituted 2,3-Dihydro-1H-isoindole ring system;

$R^{3a}$ and $R^{7a}$ are taken together with the atoms to which they are bound to form a optionally substituted six membered saturated heterocyclic ring comprising four carbons, one nitrogen atom, and a member selected from the group consisting of O, $NR^{7a}$, S, and $SO_2$;

$R^{6a}$ and $R^{7a}$ are taken together with the atoms to which they are bound to form an optionally substituted three to six membered ring consisting of all carbons and one nitrogen atom;

$R^{6a}$ and $R^{7a}$ are taken together with the atoms to which they are bound to form an optionally substituted 1,2,3,4-tetrahydro-isoquinoline ring system;

$R^{6a}$ and $R^{7a}$ are taken together with the atoms to which they are bound to form an optionally substituted 2,3-Dihydro-1H-isoindole ring system;

$R^{6a}$ and $R^{7a}$ are taken together with the atoms to which they are bound to form a optionally substituted six membered saturated heterocyclic ring consisting of four carbons, one nitrogen atom, and a member from the group including O, $NR^{7a}$, S, and $SO_2$;

$R^{8a}$ and $R^{8b}$ are each independently optionally substituted C1-C6 alkyl;

$R^9$ is selected from the group consisting of hydrogen, C1-C6 alkyl, optionally substituted phenyl, optionally substituted benzyl, and optionally substituted $CH_2CH_2Ar$;

$R^{9a}$ is selected from the group consisting of OH, C1-C6 alkoxy, and $NH_2$.

$R^{10a}$ and $R^{10b}$ are each independently is selected from the group consisting of hydrogen and optionally substituted C1-C6 alkyl;

$R^{10a}$ and $R^{10B}$ and are taken together with the atom to which they are bound to form an optionally substituted ring having 5 to 6 ring atoms;

$R^{10a}$ and $R^{10B}$ and are taken together with the atom to which they are bound to form an optionally substituted ring having 5 to 6 ring atoms containing an oxygen;

$R^{10a}$ and $R^{10B}$ and are taken together with the atom to which they are bound to form an optionally substituted ring having 5 to 6 ring atoms containing two nitrogen atoms;

$R^{11}$ is selected from the group consisting of optionally substituted phenyl and optionally substituted heteroaryl;

$R^{12}$ is C1-C6 alkyl.

Ar is selected from the group consisting of optionally substituted phenyl and optionally substituted naphthyl ring;

Ar is optionally substituted with 0-5 moieties selected from the group consisting of deuterium, halogen, trifluoromethyl, trifluoromethoxy, cyano, $NR^{7a}R^{7b}$, $CONR^{8a}R^{8b}$, C1-C6 alkyl, and C1-C6 alkoxy;

The compounds of the present invention include compounds having formula (II):

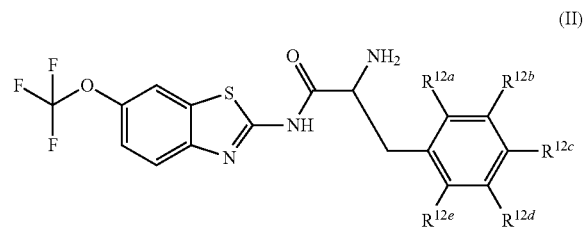

(II)

including hydrates, solvates, pharmaceutically acceptable salts, and complexes thereof, wherein:

$R^{12a}$, $R^{12b}$, $R^{12c}$, $R12^d$, and $R^{12e}$ are each independently selected from the group consisting of hydrogen, deuterium, halogen, trifluoromethyl, trifluoromethoxy, optionally substituted C1-C6 alkyl, and optionally substituted C1-C6 alkoxy;

The compounds of the present invention include compounds having formula (III):

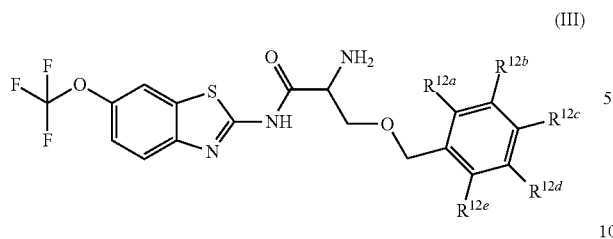

including hydrates, solvates, pharmaceutically acceptable salts, and complexes thereof, wherein:

$R^{12a}$, $R^{12b}$, $R^{12c}$, $R^{2d}$, and $R^{12e}$ are each independently selected from the group consisting of hydrogen, deuterium, halogen, trifluoromethyl, trifluoromethoxy, optionally substituted C1-C6 alkyl, and optionally substituted C1-C6 alkoxy;

The compounds of the present invention include compounds having formula (Ia):

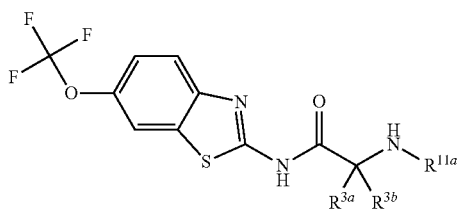

including hydrates, solvates, pharmaceutically acceptable salts, and complexes thereof, wherein:

$R^{3a}$ and $R^{3b}$ are each independently selected from the group consisting of hydrogen, optionally substituted C1-C6 alkyl, optionally substituted benzyl, optionally substituted $CH_2CH_2Ar$, optionally substituted $CH_2$heteroaryl, $CH_2OR^9$, $CH(CH_3)OR^9$, $CH_2SR^9$, $CH_2CH_2SCH_3$, $CH_2CH_2CH_2NR^{10a}R^{10b}$, $CH_2COR^{9a}$, and $CH_2CH_2COR^{9a}$;

$R^{11a}$ is selected from group consisting of optionally substituted C1-C6 alkyl, $COR^4$, and $CO_2R^4$;

$R^{11a}$ and $R^{3a}$ are taken together with the atoms to which they are bound to form a 5 membered ring.

$R^{11a}$ and $R^{3b}$ are taken together with the atoms to which they are bound to form a 5 membered ring.

The compounds of the present invention include compounds having formula (IIa):

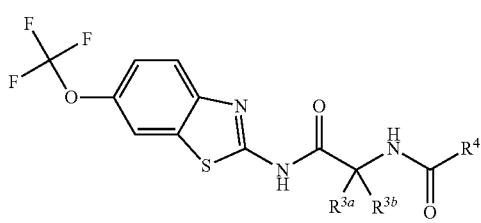

including hydrates, solvates, pharmaceutically acceptable salts, and complexes thereof.

The compounds of the present invention include compounds having formula (IIIa):

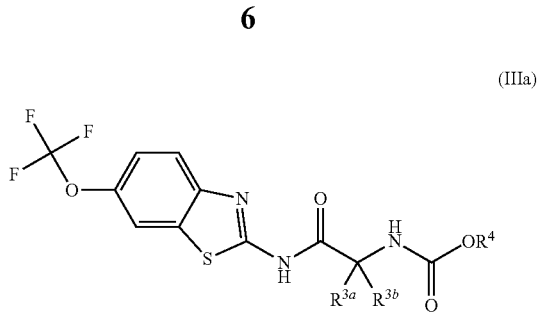

including hydrates, solvates, pharmaceutically acceptable salts, and complexes thereof.

The compounds of the present invention include compounds having formula (IVa):

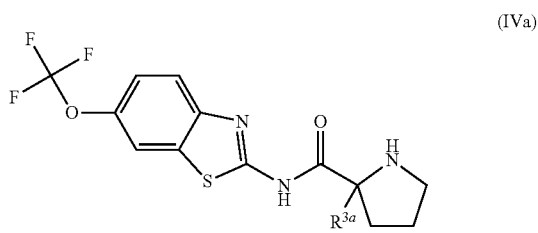

including hydrates, solvates, pharmaceutically acceptable salts, and complexes thereof.

The compounds of the present invention include compounds having formula (Va):

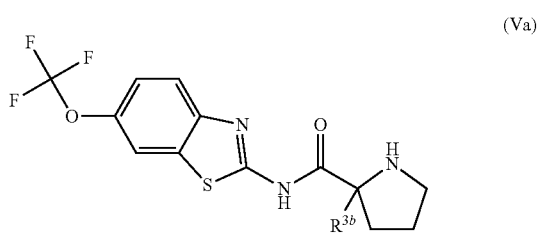

including hydrates, solvates, pharmaceutically acceptable salts, and complexes thereof.

The present invention further relates to compositions comprising: an effective amount of one or more compounds according to the present invention and an excipient.

The present invention also relates to a method for treating or preventing ALS, said method comprising administering to a subject an effective amount of a compound or composition according to the present invention.

The present invention yet further relates to a method for treating or preventing ALS, wherein said method comprises administering to a subject a composition comprising an effective amount of one or more compounds according to the present invention and an excipient.

The present invention also relates to a method for treating or preventing disease or conditions associated with ALS. Said methods comprise administering to a subject an effective amount of a compound or composition according to the present invention.

The present invention yet further relates to a method for treating or preventing disease or conditions associated with ALS, wherein said method comprises administering to a subject a composition comprising an effective amount of one or more compounds according to the present invention and an excipient.

The present invention yet further relates to a method for treating or preventing ALS.

The present invention also relates to a method for treating or preventing disease states in which riluzole is clinically relevant including, but are not limited to, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, and Huntington's disease, said method comprising administering to a subject an effective amount of a compound or composition according to the present invention.

The present invention yet further relates to a method for treating or preventing disease states in which riluzole is clinically relevant including, but are not limited to, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, and Huntington's disease, wherein said method comprises administering to a subject a composition comprising an effective amount of one or more compounds according to the present invention and an excipient.

The present invention also relates to a method for treating or preventing disease or conditions associated with disease states in which riluzole is clinically relevant including, but are not limited to, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, and Huntington's disease. Said methods comprise administering to a subject an effective amount of a compound or composition according to the present invention.

The present invention yet further relates to a method for treating or preventing disease or conditions associated with disease states in which riluzole is clinically relevant including, but are not limited to, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, and Huntington's disease, wherein said method comprises administering to a subject a composition comprising an effective amount of one or more compounds according to the present invention and an excipient.

The present invention yet further relates to a method for treating or preventing disease states in which riluzole is clinically relevant including, but are not limited to, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, and Huntington's disease.

The present invention further relates to a process for preparing the riluzole pro-drugs of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The pro-drugs of the present invention are capable of treating and preventing ALS by releasing riluzole in vivo. Pro-drugs of riluzole have enhanced stability to hepatic metabolism and are delivered into systemic circulation by oral administration, and then cleaved to release riluzole in the plasma via either an enzymatic or general biophysical release process. Riluzole (Rilutek®) is a non-toxic drug and the only FDA-approved treatment for amyotrophic lateral sclerosis (ALS or Lou Gehrig's disease) with the mild side-effect profile that riluzole has shown among ALS patients. However, the therapeutic utility of riluzole itself in ALS is very constrained by rapid first-pass metabolism in the liver and an exceptionally high level of patient-to-patient variability in the extent of the Cyp1A2-mediated oxidative metabolism that is observed. Pro-drugs of riluzole will provide more predictable pharmacokinetic properties and metabolic profiles for the parent compound. The pro-drugs of the present invention are also capable of treating and preventing disease states in which riluzole is clinically relevant including, but are not limited to, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, and Huntington's disease.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_{1-6}$alkyl)$_2$amino, the alkyl groups may be the same or different.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —CF$_3$, CF$_2$CF$_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocyclyl," whether used alone or as part of another group, are defined herein as one or more rings having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quino line. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, benzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

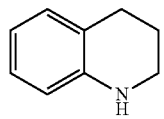

is, for the purposes of the present invention, considered a heterocyclic unit. 6,7-Dihydro-5H-cyclopentapyrimidine having the formula:

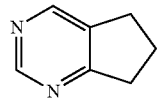

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

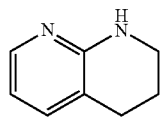

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{13}$, —SR$^{13}$, —N(R$^{13}$)$_2$, —NR$^{13}$C(O)R$^{13}$, —SO$_2$R$^{13}$, —SO$_2$OR$^{13}$, —SO$_2$N(R$^{13}$)$_2$, —C(O)R$^{13}$, —C(O)OR$^{13}$, —C(O)N(R$^{13}$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{13}$; wherein R$^{13}$, at each occurrence, independently is hydrogen, —OR$^{14}$, —SR$^{14}$, —C(O)R$^{14}$, —C(O)OR$^{14}$, —C(O)N(R$^{14}$)$_2$, —SO$_2$R$^{14}$, —S(O)$_2$OR$^{14}$, —N(R$^{14}$)$_2$, —NR$^{14}$C(O)R$^{14}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{13}$ units taken together with the atom(s) to which they are bound form an optionally substituted carbocycle or heterocycle wherein said carbocycle or heterocycle has 3 to 7 ring atoms; wherein R$^{14}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{14}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{15}$; for example, —OH, —OCH$_3$, —OCH$_2$CH$_3$, —OCH$_2$CH$_2$CH$_3$;
ii) —C(O)R$^{15}$; for example, —COCH$_3$, —COCH$_2$CH$_3$, —COCH$_2$CH$_2$CH$_3$;
iii) —C(O)OR$^{15}$; for example, —CO$_2$CH$_3$, —CO$_2$CH$_2$CH$_3$, —CO$_2$CH$_2$CH$_2$CH$_3$;
iv) —C(O)N(R$^{15}$)$_2$; for example, —CONH$_2$, —CONHCH$_3$, —CON(CH$_3$)$_2$;
v) —N(R$^{15}$)$_2$; for example, —NH$_2$, —NHCH$_3$, —N(CH$_3$)$_2$, —NH(CH$_2$CH$_3$);

vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;
viii) —SO$_2$R$^{15}$; for example, —SO$_2$H; —SO$_2$CH$_3$; —SO$_2$C$_6$H$_5$;
ix) C$_1$-C$_6$ linear, branched, or cyclic alkyl;
x) Cyano
xi) Nitro;
xii) N(R$^{15}$)C(O)R$^{15}$;
xiii) Oxo (=O);
xiv) Heterocycle; and
xv) Heteroaryl.

wherein each R$^{15}$ is independently hydrogen, optionally substituted C$_1$-C$_6$ linear or branched alkyl (e.g., optionally substituted C$_1$-C$_4$ linear or branched alkyl), or optionally substituted C$_3$-C$_6$ cycloalkyl (e.g optionally substituted C$_3$-C$_4$ cycloalkyl); or two R$^{15}$ units can be taken together to form a ring comprising 3-7 ring atoms. In certain aspects, each R$^{15}$ is independently hydrogen, C$_1$-C$_6$ linear or branched alkyl optionally substituted with halogen or C$_3$-C$_6$ cycloalkyl or C$_3$-C$_6$ cycloalkyl.

At various places in the present specification, substituents of compounds are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$, alkyl.

For the purposes of the present invention the terms "compound," "analog," and "composition of matter" stand equally well for the pro-drug agent described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include NaHCO$_3$, Na$_2$CO$_3$, KHCO$_3$, K$_2$CO$_3$, Cs$_2$CO$_3$, LiOH, NaOH, KOH, NaH$_2$PO$_4$, Na$_2$HPO$_4$, and Na$_3$PO$_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in N(R$^{13}$)$_2$, each R$^{13}$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "riluzole pro-drug" shall mean a compound that are cleaved to release riluzole in the plasma via either an enzymatic or general biophysical release process.

As used herein, the term "pro-drug agent" shall mean a compound that are cleaved to release riluzole in the plasma via either an enzymatic or general biophysical release process.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Pro-drug Agents

The pro-drug agents of the present invention are N-substituted riluzole analogs, and include all enantiomeric and diastereomeric forms and pharmaceutically accepted salts thereof having the formula (I):

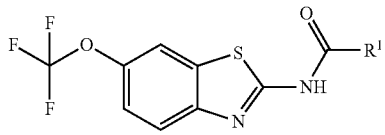

including hydrates, solvates, pharmaceutically acceptable salts, and complexes thereof, wherein:
$R^1$ is selected from the group consisting of $OR^2$, $CR^{3a}R^{3b}NH_2$, $CR^{3a}R^{3b}NR^{7a}R^{7b}$, $CH_2CH_2CO_2R^4$, $CH_2CH_2CONHR^5$, $(CR^{6a}R^{6b})_mNR^{7a}R^{7b}$, $CH_2Ar$, and optionally substituted phenyl ring; $R^2$ is selected from the group consisting of optionally substituted C1-C6 alkyl and $CH_2(CH_2)_nNR^{8a}R^{8b}$;
n=1 or 2;
$R^{3a}$ and $R^{3b}$ are each independently selected from the group consisting of hydrogen, optionally substituted C1-C6 alkyl, optionally substituted C1-C6 alkenyl, optionally substituted C1-C6 alkynyl, $CH_2R^{4a}$, optionally substituted phenyl, optionally substituted benzyl, optionally substituted $CH_2CH_2Ar$, optionally substituted $CH_2$heteroaryl $CH_2OR^9$, $CH(CH_3)OR^9$, $CH_2SR^9$, $CH_2CH_2SCH_3$, $CH_2CH_2SO_2CH_3$, $CH_2CH_2CH_2NR^{10a}R^{10b}$, $CH_2COR^{9a}$, and $CH_2CH_2COR^{9a}$;
$R^{3a}$ and $R^{3b}$ are taken together with the atom to which they are bound to form an optionally substituted three to six membered saturated heterocyclic ring comprising two to five carbon atoms and a member selected from the group consisting of O, $NR^{7a}$, S, and $SO_2$;
$R^4$ is selected from the group consisting of hydrogen and optionally substituted C1-C6 alkyl;
$R^{4a}$ is selected from the group consisting of hydrogen, optionally substituted C1-C6 Alkyl, optionally substituted C3-C6 cycloalkyl, and optionally substituted four to six membered saturated heterocyclic rings comprising three to five carbon atoms and a member selected from the group consisting of O, $NR^{7a}$, S, and $SO_2$;
$R^5$ is selected from the group consisting of hydrogen, optionally substituted C1-C6 Alkyl, $CH_2CH_2NR^{10a}R^{10b}$, and $CH_2R^{11}$;
$R^{6a}$ and $R^{6b}$ are, at each occurrence, independently selected from the group consisting of hydrogen and optionally substituted C1-C6 alkyl;
$R^{6a}$ and $R^{6b}$ are taken together with the atom to which they are bound to form an optionally substituted 6 membered ring;
m=3 or 4;
m=1 or 2;
$R^{7a}$ and $R^{7b}$ are each independently selected from the group consisting of hydrogen methyl, $COR^{12}$, and $CO_2R^{12}$;
$R^{3a}$ and $R^{7a}$ are taken together with the atoms to which they are bound to form an optionally substituted three to six membered ring consisting of all carbons and one nitrogen atom;
$R^{3a}$ and $R^{7a}$ are taken together with the atoms to which they are bound to form an optionally substituted 1,2,3,4-tetrahydro-isoquinoline ring system;
$R^{3a}$ and $R^{7a}$ are taken together with the atoms to which they are bound to form an optionally substituted 2,3-Dihydro-1H-isoindole ring system;

$R^{3a}$ and $R^{7a}$ are taken together with the atoms to which they are bound to form a optionally substituted six membered saturated heterocyclic ring comprising four carbons, one nitrogen atom, and a member selected from the group consisting of O, $NR^{7a}$, S, and $SO_2$;
$R^{6a}$ and $R^{7a}$ are taken together with the atoms to which they are bound to form an optionally substituted three to six membered ring consisting of all carbons and one nitrogen atom.
$R^{6a}$ and $R^{7a}$ are taken together with the atoms to which they are bound to form an optionally substituted 1,2,3,4-tetrahydro-isoquinoline ring system;
$R^{6a}$ and $R^{7a}$ are taken together with the atoms to which they are bound to form an optionally substituted 2,3-Dihydro-1H-isoindole ring system;
$R^{6a}$ and $R^{7a}$ are taken together with the atoms to which they are bound to form a optionally substituted six membered saturated heterocyclic ring comprising four carbons, one nitrogen atom, and a member selected from the group consisting of O, $NR^{7a}$, S, and $SO_2$;
$R^{8a}$ and $R^{8b}$ are each independently optionally substituted C1-C6 alkyl;
$R^9$ is selected from the group consisting of hydrogen, C1-C6 alkyl, optionally substituted phenyl, optionally substituted benzyl, and optionally substituted $CH_2CH_2Ar$;
$R^{9a}$ is selected from the group consisting of OH, C1-C6 alkoxy, and $NH_2$.
$R^{10a}$ and $R^{10b}$ are each independently is selected from the group consisting of hydrogen and optionally substituted C1-C6 alkyl;
$R^{10a}$ and $R^{10B}$ and are taken together with the atom to which they are bound to form an optionally substituted ring having 5 to 6 ring atoms;
$R^{10a}$ and $R^{10B}$ and are taken together with the atom to which they are bound to form an optionally substituted ring having 5 to 6 ring atoms containing an oxygen; $R^{10a}$ and $R^{10B}$ and are taken together with the atom to which they are bound to form an optionally substituted ring having 5 to 6 ring atoms containing two nitrogen atoms;
$R^{11}$ is selected from the group consisting of optionally substituted phenyl and optionally substituted heteroaryl;
$R^{12}$ is C1-C6 alkyl.
Ar is selected from the group consisting of optionally substituted phenyl and optionally substituted naphthyl ring;
Ar is optionally substituted with 0-5 moieties selected from the group consisting of deuterium, halogen, trifluoromethyl, trifluoromethoxy, cyano, $NR^{7a}R^{7b}$, $CONR^{8a}R^{8b}$, C1-C6 alkyl, and C1-C6 alkoxy;
The compounds of the present invention include compounds having formula (II):

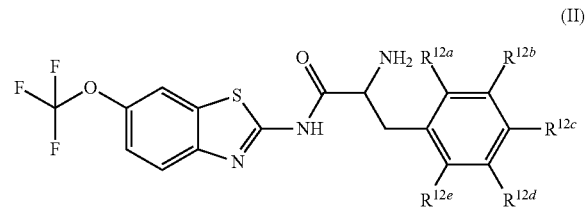

including hydrates, solvates, pharmaceutically acceptable salts, and complexes thereof, wherein:
$R^{12a}$, $R^{12b}$, $R^{12c}$, $R12^d$, and $R^{12e}$ are each independently selected from the group consisting of hydrogen, deuterium, halogen, trifluoromethyl, trifluoromethoxy, optionally substituted C1-C6 alkyl, and optionally substituted C1-C6 alkoxy;

The compounds of the present invention include compounds having formula (III):

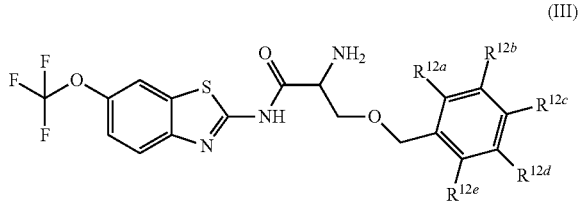

(III)

including hydrates, solvates, pharmaceutically acceptable salts, and complexes thereof, wherein:
$R^{12a}$, $R^{12b}$, $R^{12c}$, $R^{2d}$, and $R^{12e}$ are each independently selected from the group consisting of hydrogen, deuterium, halogen, trifluoromethyl, trifluoromethoxy, optionally substituted C1-C6 alkyl, and optionally substituted C1-C6 alkoxy;

The compounds of the present invention include compounds having formula (Ia):

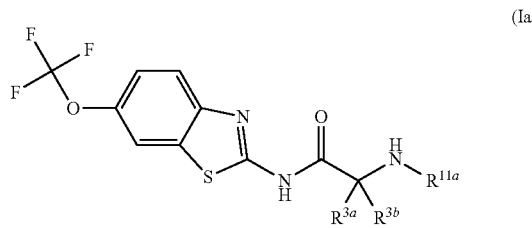

(Ia)

including hydrates, solvates, pharmaceutically acceptable salts, and complexes thereof, wherein:
$R^{3a}$ and $R^{3b}$ are each independently selected from the group consisting of hydrogen, optionally substituted C1-C6 alkyl, optionally substituted benzyl, optionally substituted $CH_2CH_2Ar$, optionally substituted $CH_2$heteroaryl, and $CH_2OR^5$;
$R^{11a}$ is selected from group consisting of optionally substituted C1-C6 alkyl, $COR^4$, and $CO_2R^4$;
$R^{11a}$ and $R^{3a}$ are taken together with the atoms to which they are bound to form a 5 membered ring.
$R^{11a}$ and $R^{3b}$ are taken together with the atoms to which they are bound to form a 5 membered ring.

The compounds of the present invention include compounds having formula (IIa):

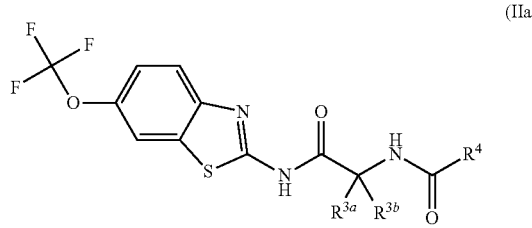

(IIa)

including hydrates, solvates, pharmaceutically acceptable salts, and complexes thereof.

The compounds of the present invention include compounds having formula (IIIa):

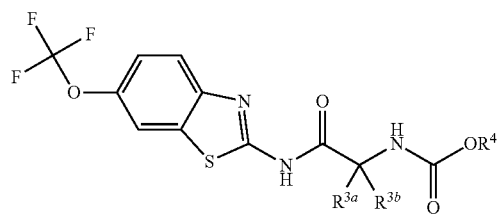

(IIIa)

including hydrates, solvates, pharmaceutically acceptable salts, and complexes thereof.

The compounds of the present invention include compounds having formula (IVa):

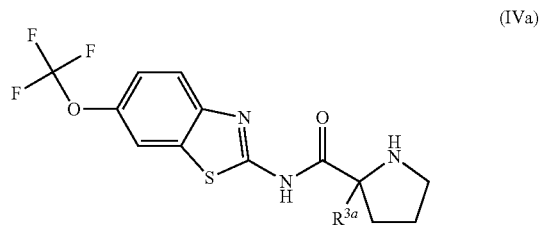

(IVa)

including hydrates, solvates, pharmaceutically acceptable salts, and complexes thereof.

The compounds of the present invention include compounds having formula (Va):

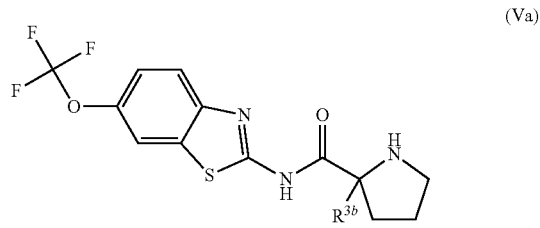

(Va)

including hydrates, solvates, pharmaceutically acceptable salts, and complexes thereof.

In some embodiments $R^1$ is $OR^2$.

In some embodiments $R^1$ is $CR^{3a}R^{3b}NH_2$.

In some embodiments $R^1$ is $CR^{3a}R^{3b}NR^{7a}R^{7b}$.

In some embodiments $R^1$ is $CH_2CH_2CO_2R^4$.

In some embodiments $R^1$ is $CH_2CH_2CONHR^5$.

In some embodiments $R^1$ is $(CR^{6a}R^{6b})_mNR^{7a}R^{7b}$

In some embodiments $R^1$ is $CH_2Ar$.

In some embodiments $R^1$ is an optionally substituted phenyl ring.

In some embodiments $R^1$ is $(CH_2)_4NHCH_3$.

In some embodiments $R^1$ is $(CH_2)_4NH_2$.

In some embodiments $R^1$ is $CH_2$-2-nitrophenyl.

In some embodiments $R^1$ is 4-aminophenyl.

In some embodiments $R^1$ is

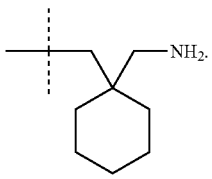

In some embodiments $R^2$ is optionally substituted C1-C6 alkyl.
In some embodiments $R^2$ is $CH_2(CH_2)_nNR^{8a}R^{8b}$.
In some embodiments $R^2$ is $CH_2CH_2NR^{8a}R^{8b}$.
In some embodiments $R^2$ is $CH_2(CH_2)_2NR^{8a}R^{8b}$.
In some embodiments $R^2$ is $CH_3$.
In some embodiments $R^2$ is $CH_2CH_3$.
In some embodiments $R^2$ is $(CH_2)_2CH_3$.
In some embodiments $R^2$ is $(CH_2)_3CH_3$.
In some embodiments $R^2$ is $CH_2CH(CH_3)_2$.
In some embodiments $R^2$ is $(CH_2)_5CH_3$.
In some embodiments $R^2$ is $(CH_2)_2N(CH_3)_2$.
In some embodiments $R^2$ is $(CH_2)_3N(CH_3)_2$.
In some embodiments n is 1.
In some embodiments n is 2.
In some embodiments $R^{3a}$ is hydrogen.
In some embodiments $R^{3a}$ is optionally substituted C1-C6 alkyl.
In some embodiments $R^{3a}$ is optionally substituted C1-C6 alkenyl.
In some embodiments $R^{3a}$ is optionally substituted C1-C6 alkynyl.
In some embodiments $R^{3a}$ is $CH_2R^{4a}$.
In some embodiments $R^{3a}$ is optionally substituted phenyl.
In some embodiments $R^{3a}$ is optionally substituted benzyl.
In some embodiments $R^{3a}$ is optionally substituted $CH_2CH_2Ar$.
In some embodiments $R^{3a}$ is optionally substituted $CH_2$heteroaryl.
In some embodiments $R^{3a}$ is $CH_2OR^9$.
In some embodiments $R^{3a}$ is $CH(CH_3)OR^9$.
In some embodiments $R^{3a}$ is $CH_2SR^9$.
In some embodiments $R^{3a}$ is $CH_2CH_2SCH_3$.
In some embodiments $R^{3a}$ is $CH_2CH_2SO_2CH_3$.
In some embodiments $R^{3a}$ is $CH_2CH_2CH_2NR^{10a}R^{10b}$.
In some embodiments $R^{3a}$ is $CH_2COR^{9a}$.
In some embodiments $R^{3a}$ is $CH_2CH_2COR^{9a}$.
In some embodiments $R^{3a}$ is $CH_3$.
In some embodiments $R^{3a}$ is $CH(CH_3)_2$.
In some embodiments $R^{3a}$ is $CH_2Ph$.
In some embodiments $R^{3a}$ is $CH_2OCH_2Ph$.
In some embodiments $R^{3a}$ is $CH_2CH(CH_3)_2$.
In some embodiments $R^{3b}$ is hydrogen.
In some embodiments $R^{3b}$ is optionally substituted C1-C6 alkyl.
In some embodiments $R^{3b}$ is optionally substituted C1-C6 alkenyl.
In some embodiments $R^{3b}$ is optionally substituted C1-C6 alkynyl.
In some embodiments $R^{3b}$ is $CH_2R^{4a}$.
In some embodiments $R^{3b}$ is optionally substituted phenyl.
In some embodiments $R^{3b}$ is optionally substituted benzyl.
In some embodiments $R^{3b}$ is optionally substituted $CH_2CH_2Ar$.
In some embodiments $R^{3b}$ is optionally substituted $CH_2$heteroaryl.
In some embodiments $R^{3b}$ is $CH_2OR^9$.
In some embodiments $R^{3b}$ is $CH(CH_3)OR^9$.
In some embodiments $R^{3b}$ is $CH_2SR^9$.
In some embodiments $R^{3b}$ is $CH_2CH_2SCH_3$.
In some embodiments $R^{3b}$ is $CH_2CH_2SO_2CH_3$.
In some embodiments $R^{3b}$ is $CH_2CH_2CH_2NR^{10a}R^{10b}$.
In some embodiments $R^{3b}$ is $CH_2COR^{9a}$.
In some embodiments $R^{3b}$ is $CH_2CH_2COR^{9a}$.
In some embodiments $R^{3b}$ is $CH_3$.
In some embodiments $R^{3b}$ is $CH(CH_3)_2$.
In some embodiments $R^{3b}$ is $CH_2Ph$.
In some embodiments $R^{3b}$ is $CH_2OCH_2Ph$.
In some embodiments $R^{3b}$ is $CH_2CH(CH_3)_2$.
In some embodiments $R^{3a}$ and $R^{3b}$ are taken together with the atom to which they are bound to form an optionally substituted three to six membered saturated heterocyclic ring comprising two to five carbon atoms and a member selected from the group consisting of O, $NR^{7a}$, S and, $SO_2$;
In some embodiments $R^4$ is hydrogen.
In some embodiments $R^4$ is optionally substituted C1-C6 alkyl.
In some embodiments $R^4$ is $CH_3$.
In some embodiments $R^4$ is $C(CH_3)_3$.
In some embodiments $R^{4a}$ is hydrogen.
In some embodiments $R^{4a}$ is optionally substituted C1-C6 alkyl.
In some embodiments $R^{4a}$ is optionally substituted C3-C6 cycloalkyl.
In some embodiments $R^{4a}$ is optionally substituted four to six membered saturated heterocyclic ring comprising three to five carbon atoms and a member selected from the group consisting of O, $NR^{7a}$, S, and $SO_2$;
In some embodiments $R^5$ is hydrogen.
In some embodiments $R^5$ is optionally substituted C1-C6 Alkyl.
In some embodiments $R^5$ is $CH_2CH_2NR^{10a}R^{10b}$.
In some embodiments $R^5$ is $CH_2R^{11}$.
In some embodiments $R^5$ is $CH_2$-3-pyridyl.
In some embodiments $R^5$ is

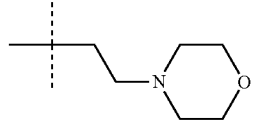

In some embodiments $R^{6a}$ is hydrogen.
In some embodiments $R^{6a}$ is optionally substituted C1-C6 alkyl.
In some embodiments $R^{6b}$ is hydrogen.
In some embodiments $R^{6b}$ is optionally substituted C1-C6 alkyl.
In some embodiments $R^{6a}$ and $R^{6b}$ are taken together with the atom to which they are bound to form an optionally substituted 6 membered ring.
In some embodiments m is 1.
In some embodiments m is 2.
In some embodiments m is 3.
In some embodiments m is 4.
In some embodiments $R^{7a}$ is hydrogen.
In some embodiments $R^{7a}$ is methyl.

In some embodiments $R^{7a}$ is $COR^{12}$.
In some embodiments $R^{7a}$ is $CO2R^{12}$.
In some embodiments $R^{7b}$ is hydrogen.
In some embodiments $R^{7b}$ is methyl.
In some embodiments $R^{7b}$ is $COR^{12}$.
In some embodiments $R^{7b}$ is $CO2R^{12}$.
In some embodiments $R^{3a}$ and $R^{7a}$ taken together can form a three membered ring consisting of all carbons and one nitrogen atom.
In some embodiments $R^{3a}$ and $R^{7a}$ taken together can form a four membered ring consisting of all carbons and one nitrogen atom.
In some embodiments $R^{3a}$ and $R^{7a}$ taken together can form a five membered ring consisting of all carbons and one nitrogen atom.
In some embodiments $R^{3a}$ and $R^{7a}$ taken together can form a six membered ring consisting of all carbons and one nitrogen atom.
In some embodiments $R^{3a}$ and $R^{7a}$ are taken together with the atoms to which they are bound to form an optionally substituted 1,2,3,4-tetrahydro-isoquinoline ring system.
In some embodiments $R^{3a}$ and $R^{7a}$ are taken together with the atoms to which they are bound to form an optionally substituted 2,3-Dihydro-1H-isoindole ring system;
In some embodiments $R^{3a}$ and $R^{7a}$ are taken together with the atoms to which they are bound to form a optionally substituted six membered saturated heterocyclic ring comprising four carbons, one nitrogen atom, and a member selected from the group consisting of O, $NR^{7a}$, S, and $SO_2$.
In some embodiments $R^{6a}$ and $R^{7a}$ taken together can form a three membered ring consisting of all carbons and one nitrogen atom.
In some embodiments $R^{6a}$ and $R^{7a}$ taken together can form a four membered ring consisting of all carbons and one nitrogen atom.
In some embodiments $R^{6a}$ and $R^{7a}$ taken together can form a five membered ring consisting of all carbons and one nitrogen atom.
In some embodiments $R^{6a}$ and $R^{7a}$ taken together can form a six membered ring consisting of all carbons and one nitrogen atom.
In some embodiments $R^{6a}$ and $R^{7a}$ are taken together with the atoms to which they are bound to form an optionally substituted 1,2,3,4-tetrahydro-isoquinoline ring system.
In some embodiments $R^{6a}$ and $R^{7a}$ are taken together with the atoms to which they are bound to form an optionally substituted 2,3-Dihydro-1H-isoindole ring system;
In some embodiments $R^{6a}$ and $R^{7a}$ are taken together with the atoms to which they are bound to form a optionally substituted six membered saturated heterocyclic ring comprising four carbons, one nitrogen atom, and a member selected from the group consisting of O, $NR^{7a}$, S, and $SO_2$.
In some embodiments $R^{8a}$ is optionally substituted C1-C6 alkyl.
In some embodiments $R^{8b}$ is optionally substituted C1-C6 alkyl.
In some embodiments $R^9$ is hydrogen.
In some embodiments $R^9$ is C1-C6 alkyl.
In some embodiments $R^9$ is optionally substituted phenyl.
In some embodiments $R^9$ is optionally substituted benzyl.
In some embodiments $R^9$ is optionally substituted $CH_2CH_2Ar$.
In some embodiments $R^{9a}$ is OH.
In some embodiments $R^{9a}$ is C1-C6 alkoxy.
In some embodiments $R^{9a}$ is $NH_2$.
In some embodiments $R^{10a}$ is hydrogen.

In some embodiments $R^{10a}$ is optionally substituted C1-C6 alkyl.
In some embodiments $R^{10a}$ is hydrogen.
In some embodiments $R^{10a}$ is optionally substituted C1-C6 alkyl.
In some embodiments $R^{10a}$ and $R^{10B}$ and are taken together with the atom to which they are bound to form an optionally substituted 5 membered ring.
In some embodiments $R^{10a}$ and $R^{10B}$ and are taken together with the atom to which they are bound to form an optionally substituted 5 membered ring containing an oxygen atom.
In some embodiments $R^{10a}$ and $R^{10B}$ and are taken together with the atom to which they are bound to form an optionally substituted 5 membered ring containing two nitrogen atoms.
In some embodiments $R^{10a}$ and $R^{10B}$ and are taken together with the atom to which they are bound to form an optionally substituted 6 membered ring.
In some embodiments $R^{10a}$ and $R^{10B}$ and are taken together with the atom to which they are bound to form an optionally substituted 6 membered ring containing an oxygen atom.
In some embodiments $R^{10a}$ and $R^{10B}$ and are taken together with the atom to which they are bound to form an optionally substituted 6 membered ring containing two nitrogen atoms.
In some embodiments $R^{11}$ is optionally substituted phenyl.
In some embodiments $R^{11}$ is optionally substituted heteroaryl.
In some embodiments $R^{12}$ is C1-C6 alkyl.
In some embodiments Ar is optionally substituted phenyl.
In some embodiments Ar is optionally substituted napthyl.
In some embodiments Ar is optionally substituted with 1, 2, 3, 4 or 5 substituents independently selected from deuterium, halogen, trifluoromethyl, trifluoromethoxy, cyano, $NR^{7a}R^{7b}$, $CONR^{8a}R^{8b}$, C1-C6 alkyl, and C1-C6 alkoxy.
In some embodiments $R^{12a}$ is hydrogen.
In some embodiments $R^{12a}$ is deuterium.
In some embodiments $R^{12a}$ is optionally substituted C1-C6 alkyl.
In some embodiments $R^{12a}$ is optionally substituted C1-C6 alkoxy.
In some embodiments $R^{12a}$ is halogen.
In some embodiments $R^{12a}$ is fluorine, chlorine, methyl, methoxy, trifluoromethyl, or trifluoromethoxy.
In some embodiments $R^{12b}$ is hydrogen.
In some embodiments $R^{12b}$ is deuterium.
In some embodiments $R^{12b}$ is optionally substituted C1-C6 alkyl.
In some embodiments $R^{12b}$ is optionally substituted C1-C6 alkoxy.
In some embodiments $R^{12b}$ is halogen.
In some embodiments $R^{12b}$ is fluorine, chlorine, methyl, methoxy, trifluoromethyl, or trifluoromethoxy.
In some embodiments $R^{12c}$ is hydrogen.
In some embodiments $R^{12c}$ is deuterium.
In some embodiments $R^{12c}$ is optionally substituted C1-C6 alkyl.
In some embodiments $R^{12c}$ is optionally substituted C1-C6 alkoxy.
In some embodiments $R^{12c}$ is halogen.
In some embodiments $R^{12c}$ is fluorine, chlorine, methyl, methoxy, trifluoromethyl, or trifluoromethoxy.

In some embodiments $R^{12d}$ is hydrogen.
In some embodiments $R^{12d}$ is deuterium.
In some embodiments $R^{12d}$ is optionally substituted C1-C6 alkyl.
In some embodiments $R^{12d}$ is optionally substituted C1-C6 alkoxy.
In some embodiments $R^{12d}$ is halogen.
In some embodiments $R^{12d}$ is fluorine, chlorine, methyl, methoxy, trifluoromethyl, or trifluoromethoxy.
In some embodiments $R^{12e}$ is hydrogen.
In some embodiments $R^{12e}$ is deuterium.
In some embodiments $R^{12e}$ is optionally substituted C1-C6 alkyl.
In some embodiments $R^{12e}$ is optionally substituted C1-C6 alkoxy.
In some embodiments $R^{12e}$ is halogen.
In some embodiments $R^{12e}$ is fluorine, chlorine, methyl, methoxy, trifluoromethyl, or trifluoromethoxy.
In some embodiments $R^{11a}$ is optionally substituted C1-C6 alkyl.
In some embodiments $R^{11a}$ is $COR^4$.
In some embodiments $R^{11a}$ is $CO_2R^4$.
In some embodiments $R^{11a}$ and $R^{3a}$ are taken together with the atoms to which they are bound to form a 5 membered ring.
In some embodiments $R^{11a}$ and $R^{3b}$ are taken together with the atoms to which they are bound to form a 5 membered ring.

Exemplary embodiments include compounds having the formula (I) or a pharmaceutically acceptable salt form thereof:

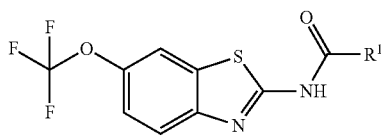

(I)

wherein non-limiting examples of $R^1$ are defined herein below in Table 1.

TABLE 1

| Entry | $R^1$ |
|---|---|
| 1 | $(CH_2)_4NHCH_3$ |
| 2 | $(CH_2)_4NH_2$ |
| 3 | ![structure] |
| 4 | ![structure] |
| 5 | ![structure] |
| 6 | ![structure] |
| 7 | ![structure] |
| 8 | ![structure] |
| 9 | ![structure] |
| 10 | ![structure] |
| 11 | ![structure] |
| 12 | ![structure] |
| 13 | ![structure] |
| 14 | ![structure] |
| 15 | $CH_2$-2-nitrophenyl |

TABLE 1-continued

| Entry | R¹ |
|---|---|
| 16 | 4-aminophenyl |
| 17 | (S)-piperidin-2-yl |
| 18 | (R)-piperidin-2-yl |
| 19 | (S)-morpholin-3-yl |
| 20 | (R)-morpholin-3-yl |
| 21 | (S)-piperazin-2-yl |
| 22 | (R)-piperazin-2-yl |
| 21 | (S)-1-methylpiperazin-2-yl |
| 22 | (R)-1-methylpiperazin-2-yl |
| 23 | (R)-1,1-dioxothiomorpholin-3-yl |
| 24 | 4-amino-tetrahydropyran-4-yl |
| 25 | 4-amino-1-methylpiperidin-4-yl |
| 26 | 4-amino-1,1-dioxothiopyran-4-yl |

Exemplary embodiments include compounds having the formula (IV) or a pharmaceutically acceptable salt form thereof:

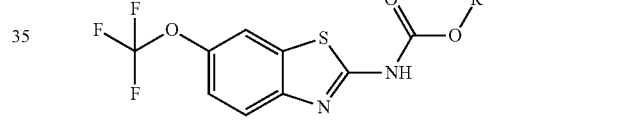

(IV)

wherein non-limiting examples of R² are defined herein below in Table 2.

TABLE 2

| Entry | R² |
|---|---|
| 1 | $CH_3$ |
| 2 | $CH_2CH_3$ |
| 3 | $(CH_2)_2CH_3$ |
| 4 | $(CH_2)_3CH_3$ |
| 5 | $CH_2CH(CH_3)_2$ |
| 6 | $(CH_2)_4CH_3$ |
| 7 | $(CH_2)_5CH_3$ |
| 8 | $(CH_2)_2N(CH_3)_2$ |
| 9 | $(CH_2)_3N(CH_3)_2$ |

Exemplary embodiments include compounds having the formula (V) or a pharmaceutically acceptable salt form thereof:

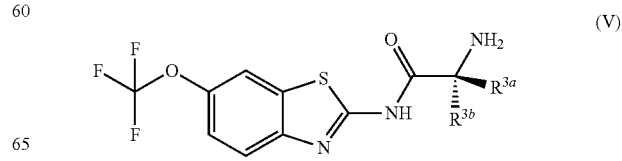

(V)

wherein non-limiting examples of $R^{3a}$ and $R^{3b}$ are defined herein below in Table 3

TABLE 3

| Entry | $R^{3a}$ | $R^{3b}$ |
|---|---|---|
| 1 | H | H |
| 2 | H | $CH_3$ |
| 3 | H | $CH(CH_3)_2$ |
| 4 | H | $CH_2Ph$ |
| 5 | H | $CH_2OCH_2Ph$ |
| 6 | H | $CH_2CH(CH_3)_2$ |
| 7 | $CH_3$ | H |
| 8 | $CH(CH_3)_2$ | H |
| 9 | $CH_2Ph$ | H |
| 10 | $CH_2OCH_2Ph$ | H |
| 11 | $CH_2CH(CH_3)_2$ | H |
| 12 | H | $CH_2OCH_3$ |
| 13 | $CH_2OCH_3$ | H |
| 14 | H | $CH_2OC(CH_3)_3$ |
| 15 | $CH_2OC(CH_3)_3$ | H |
| 16 | $CH(CH_3)CH_2CH_3$ | H |
| 17 | H | $CH(CH_3)CH_2CH_3$ |
| 18 | $CH_3$ | $CH_3$ |

Exemplary embodiments include compounds having the formula (VI) or a pharmaceutically acceptable salt form thereof:

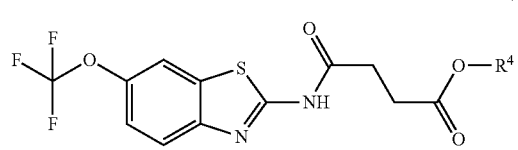

(VI)

wherein non-limiting examples of $R^4$ are defined herein below in Table 4.

TABLE 4

| Entry | $R^4$ |
|---|---|
| 1 | H |
| 2 | $CH_3$ |
| 3 | $C(CH_3)_3$ |

Exemplary embodiments include compounds having the formula (VII) or a pharmaceutically acceptable salt form thereof:

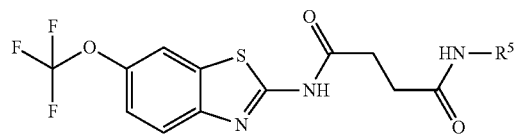

(VII)

wherein non-limiting examples of $R^5$ are defined herein below in Table 5.

TABLE 5

| Entry | $R^5$ |
|---|---|
| 1 | $CH_2$-3-pyridyl |
| 2 | 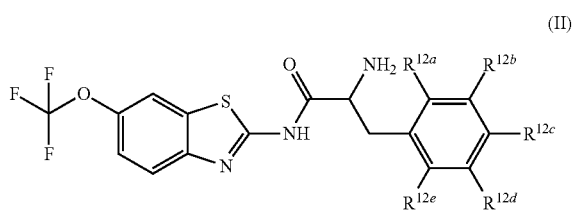 |

Exemplary embodiments include compounds having the formula (II) or a pharmaceutically acceptable salt form thereof:

(II)

wherein non-limiting examples of $R^{12a}$, $R^{12b}$, $R^{12c}$, $R^{12d}$, and $R^{12e}$ are defined herein below in Table 6.

TABLE 6

| Entry | $R^{12a}$ | $R^{12b}$ | $R^{12c}$ | $R^{12d}$ | $R^{12e}$ |
|---|---|---|---|---|---|
| 1 | F | H | H | H | H |
| 2 | H | F | H | H | H |
| 3 | H | H | F | H | H |
| 4 | Cl | H | H | H | H |
| 5 | H | Cl | H | H | H |
| 6 | H | H | Cl | H | H |
| 7 | $OCF_3$ | H | H | H | H |
| 8 | H | $OCF_3$ | H | H | H |
| 9 | H | H | $OCF_3$ | H | H |
| 10 | H | H | D | H | H |
| 11 | $CH_3$ | H | H | H | H |
| 12 | H | $CH_3$ | H | H | H |
| 13 | H | H | $CH_3$ | H | H |
| 14 | $CF_3$ | H | H | H | H |
| 15 | H | $CF_3$ | H | H | H |
| 16 | H | H | $CF_3$ | H | H |
| 17 | $OCF_3$ | H | H | H | H |
| 18 | H | $OCF_3$ | H | H | H |
| 19 | H | H | $OCF_3$ | H | H |
| 20 | $OCH_3$ | H | H | H | H |
| 21 | H | $OCH_3$ | H | H | H |
| 22 | H | H | $OCH_3$ | H | H |
| 23 | F | F | H | H | H |
| 24 | H | F | F | H | H |
| 25 | F | H | F | H | H |
| 26 | Cl | Cl | H | H | H |
| 27 | Cl | H | Cl | H | H |
| 28 | H | Cl | Cl | H | H |
| 29 | $OCF_3$ | F | H | H | H |
| 30 | D | D | D | D | D |
| 31 | $CH_3$ | $CH_3$ | H | H | H |
| 32 | $CF_3$ | F | H | H | H |
| 33 | $OCF_3$ | F | H | H | H |
| 34 | $OCH_3$ | F | H | H | H |

Exemplary embodiments include compounds having the formula (III) or a pharmaceutically acceptable salt form thereof:

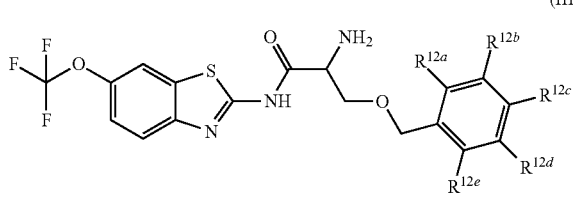

(III)

wherein non-limiting examples of $R^{12a}$, $R^{12b}$, $R^{12c}$, $R^{12d}$, and $R^{12e}$ are defined herein below in Table 7.

TABLE 7

| Entry | $R^{12a}$ | $R^{12b}$ | $R^{12c}$ | $R^{12d}$ | $R^{12e}$ |
|---|---|---|---|---|---|
| 1 | F | H | H | H | H |
| 2 | H | F | H | H | H |
| 3 | H | H | F | H | H |
| 4 | Cl | H | H | H | H |
| 5 | H | Cl | H | H | H |
| 6 | H | H | Cl | H | H |
| 7 | $OCF_3$ | H | H | H | H |
| 8 | H | $OCF_3$ | H | H | H |
| 9 | H | H | $OCF_3$ | H | H |
| 10 | H | H | D | H | H |
| 11 | $CH_3$ | H | H | H | H |
| 12 | H | $CH_3$ | H | H | H |
| 13 | H | H | $CH_3$ | H | H |
| 14 | $CF_3$ | H | H | H | H |
| 15 | H | $CF_3$ | H | H | H |
| 16 | H | H | $CF_3$ | H | H |
| 17 | $OCH_3$ | H | H | H | H |
| 18 | H | $OCH_3$ | H | H | H |
| 19 | H | H | $OCH_3$ | H | H |
| 20 | F | F | H | H | H |
| 21 | F | H | F | H | H |
| 22 | H | F | F | H | H |
| 23 | Cl | Cl | H | H | H |
| 24 | Cl | H | Cl | H | H |
| 25 | H | Cl | Cl | H | H |
| 26 | $OCF_3$ | F | H | H | H |
| 27 | D | D | D | D | D |
| 28 | $CH_3$ | $CH_3$ | H | H | H |
| 29 | $CF_3$ | F | H | H | H |
| 30 | $OCF_3$ | F | H | H | H |
| 31 | $OCH_3$ | F | H | H | H |

Exemplary embodiments include compounds having the formula (Ia) or a pharmaceutically acceptable salt form thereof:

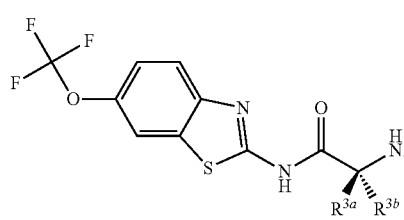

(Ia)

wherein non-limiting examples of $R^{3a}$, $R^{3b}$, and $R^{11a}$ are defined herein below in Table 8.

TABLE 8

| Entry | $R^{3a}$ | $R^{11a}$ | $R^{3b}$ |
|---|---|---|---|
| 1 | $CH_2CO_2H$ | H | H |
| 2 | $CH_2CONH_2$ | H | H |

TABLE 8-continued

| Entry | $R^{3a}$ | $R^{11a}$ | $R^{3b}$ |
|---|---|---|---|
| 3 | $CH_2CH_2CO_2H$ | H | H |
| 4 | $CH_2CH_2CONH_2$ | H | H |
| 5 | $CH_2CH_2SCH_3$ | H | H |
| 6 | $CH_2CH_2SO_2CH_3$ | H | H |
| 7 | H | H | $CH_2CO_2H$ |
| 8 | H | H | $CH_2CONH_2$ |
| 9 | H | H | $CH_2CH_2CO_2H$ |
| 10 | H | H | $CH_2CH_2CONH_2$ |
| 11 | H | H | $CH_2CH_2SCH_3$ |
| 12 | H | H | $CH_2CH_2SO_2CH_3$ |
| 13 | cyclohexyl | H | H |
| 14 | 4-tetrahydropyranyl | H | H |
| 15 | 4-piperidinyl (NH) | H | H |
| 16 | 1-methyl-4-piperidinyl | H | H |
| 17 | 4-tetrahydrothiopyranyl | H | H |
| 18 | 4-(1,1-dioxo-tetrahydrothiopyranyl) | H | H |
| 19 | H | H | cyclohexyl |
| 20 | H | H | 4-tetrahydropyranyl |
| 21 | H | H | 4-piperidinyl (NH) |

TABLE 8-continued

| Entry | $R^{3a}$ | $R^{11a}$ | $R^{3b}$ |
|---|---|---|---|
| 22 | H | H | (N-methylpiperidinyl) |
| 23 | H | H | (tetrahydrothiopyranyl) |
| 24 | H | H | (tetrahydrothiopyranyl-SO$_2$) |
| 25 | H | COCH$_3$ | H |
| 26 | H | COCH$_3$ | CH$_3$ |
| 27 | H | COCH$_3$ | CH(CH$_3$)$_2$ |
| 28 | H | COCH$_3$ | CH$_2$Ph |
| 29 | H | COCH$_3$ | CH$_2$OCH$_2$Ph |
| 30 | H | COCH$_3$ | CH$_2$CH(CH$_3$)$_2$ |
| 31 | CH$_3$ | COCH$_3$ | H |
| 32 | CH(CH$_3$)$_2$ | COCH$_3$ | H |
| 33 | CH$_2$Ph | COCH$_3$ | H |
| 34 | CH$_2$OCH$_2$Ph | COCH$_3$ | H |
| 35 | CH$_2$CH(CH$_3$)$_2$ | COCH$_3$ | H |
| 36 | H | CO$_2$C(CH$_3$)$_3$ | H |
| 37 | H | CO$_2$C(CH$_3$)$_3$ | CH$_3$ |
| 38 | H | CO$_2$C(CH$_3$)$_3$ | CH(CH$_3$)$_2$ |
| 39 | H | CO$_2$C(CH$_3$)$_3$ | CH$_2$Ph |
| 40 | H | CO$_2$C(CH$_3$)$_3$ | CH$_2$OCH$_2$Ph |
| 41 | H | CO$_2$C(CH$_3$)$_3$ | CH$_2$CH(CH$_3$)$_2$ |
| 42 | CH$_3$ | CO$_2$C(CH$_3$)$_3$ | H |
| 43 | CH(CH$_3$)$_2$ | CO$_2$C(CH$_3$)$_3$ | H |
| 44 | CH$_2$Ph | CO$_2$C(CH$_3$)$_3$ | H |
| 45 | CH$_2$OCH$_2$Ph | CO$_2$C(CH$_3$)$_3$ | H |
| 46 | CH$_2$CH(CH$_3$)$_2$ | CO$_2$C(CH$_3$)$_3$ | H |
| 47 | —CH$_2$CH$_2$CH$_2$— | | H |
| 48 | H | | —CH$_2$CH$_2$CH$_2$— |

For the purposes of the present invention, a compound depicted by the racemic formula will stand equally well for either of the two enantiomers or mixtures thereof, or in the case where a second chiral center is present, all diastereomers.

For the purposes of demonstrating the manner in which the compounds of the present invention are named and referred to herein, the compound having the formula:

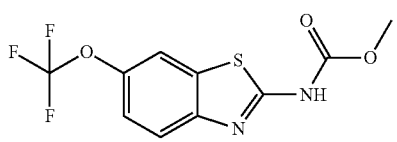 [SMILES: COC(=O)Nc1nc2ccc(OC(F)(F)F)cc2s1]

has the chemical name (6-trifluoromethoxy-benzothiazol-2-yl)-carbamic acid methyl ester.

For the purposes of demonstrating the manner in which the compounds of the present invention are named and referred to herein, the compound having the formula:

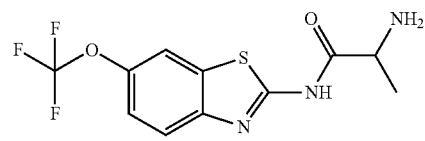 [SMILES: CC(N)C(=O)Nc1nc2ccc(OC(F)(F)F)cc2s1]

has the chemical name (6-trifluoromethoxy-benzothiazol-2-yl)-carbamic acid methyl ester.

For the purposes of demonstrating the manner in which the compounds of the present invention are named and referred to herein, the compound having the formula:

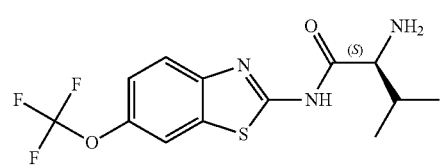

has the chemical name (S)-2-amino-3-methyl-N-(6-trifluoromethoxy-benzothiazol-2-yl)-butyramide.

For the purposes of the present invention, a compound depicted by the racemic formula, for example:

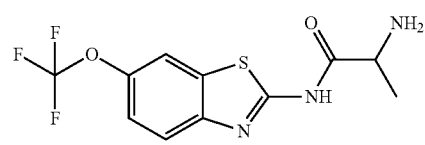 [SMILES: CC(N)C(=O)Nc1nc2ccc(OC(F)(F)F)cc2s1]

will stand equally well for either of the two enantiomers having the formula:

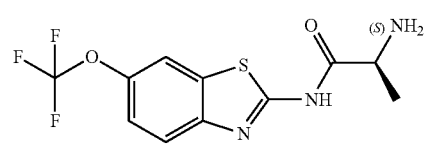

or the formula:

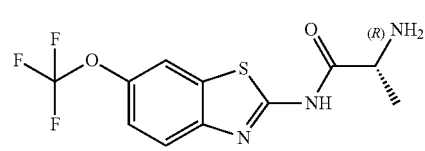

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

PROCESS

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in Scheme 1.

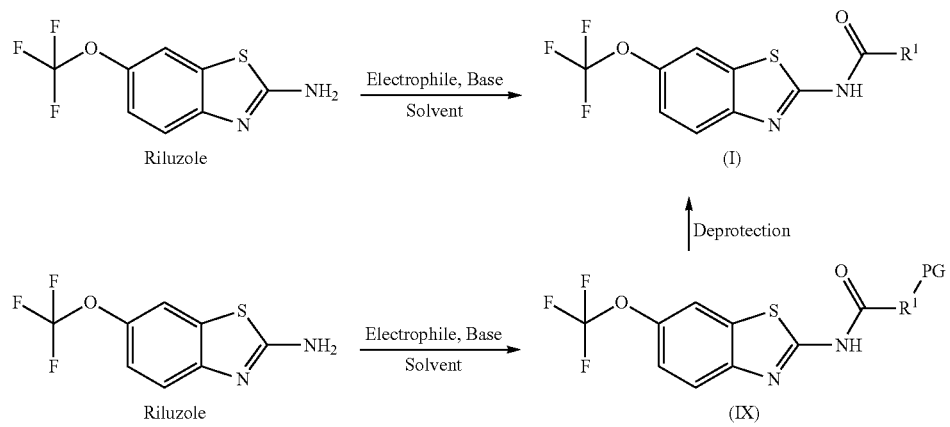

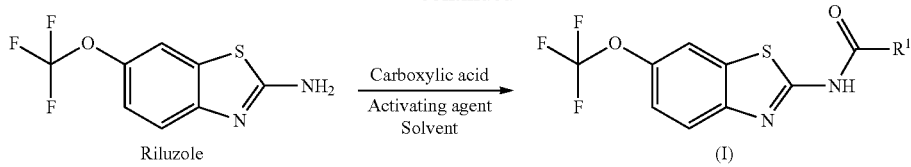

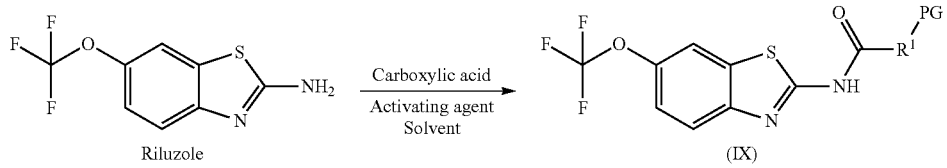

Riluzole, a known compound, is reacted with an electrophile such as an acid chloride, acid anhydride, a chloroformate, and the like, in a suitable solvent such as N,N-dimethylformamide, 1,4-dioxane, tetrahydrofuran, methylene chloride and the like in the presence of a suitable base such as triethylamine, diisopropylamine, or N-methylmorpholine and the like, to give compounds of formula (I) directly or a compound of the formula (IX). Alternatively, Riluzole is reacted with a carboxylic acid in the presence of an activating agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, and the like. in a suitable solvent such as N,N-dimethylformamide, 1,4-dioxane, tetrahydrofuran, methylene chloride and the like, optionally in the presence of a suitable base such as triethylamine, diisopropylamine, N-methylmorpholine, pyridine, and the like, to give compounds of formula (I) directly or a compound of the formula (IX).

Compounds of the formula (IX) can be converted by compounds of the formula (I) by removal of the protecting group. The protecting group can be remove by treatment under suitable conditions such as 1) with acid, such as hydrogen chloride, trifluoroacetic acid, and the like in organic solvent such as 1,4-dioxane, dichloromethane, and the like, or 2) hydrogen in the presence of a catalyst such as palladium on activated carbon, platinum oxide and the like in an organic solvent such as ethyl acetate, methanol, ethanol or 3) base such as lithium hydroxide, sodium hydroxide, potassium carbonate and the like in a solvent like water, methanol, tetrahydrofuran and the like to provide compounds of the formula (I).

Compounds of formula (Ia) may be prepared according to the process outlined in Scheme 2.

Scheme 2

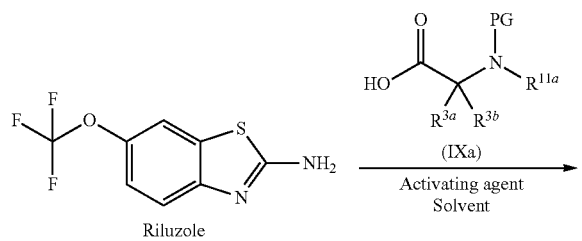

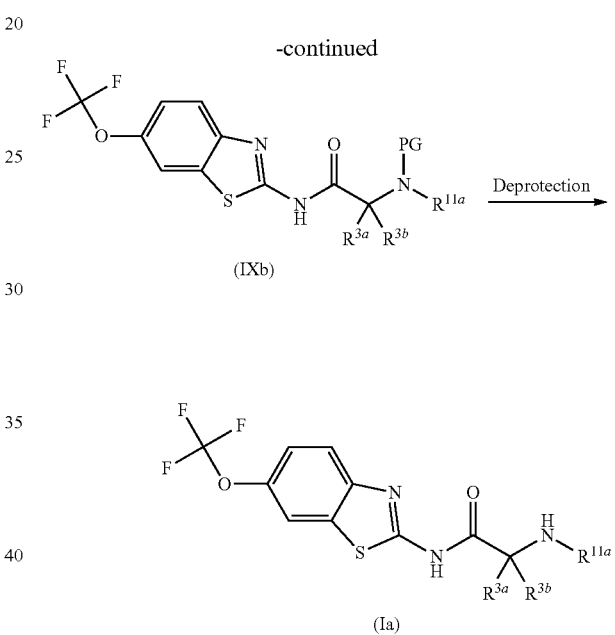

Riluzole is reacted with a compound of the formula (IXa) wherein PG is a suitable protecting group in the presence of an activating agent such as O-(benzotriazol-1-yl)-N,N,N',N'-tetramethyluronium hexafluorophosphate, N,N'-dicyclohexylcarbodiimide, 1-ethyl-3-(3-dimethylaminopropyl) carbodiimide, and the like. in a suitable solvent such as N,N-dimethylformamide, 1,4-dioxane, tetrahydrofuran, methylene chloride and the like, optionally in the presence of a suitable base such as triethylamine, diisopropylamine, N-methylmorpholine, pyridine, and the like, to give compounds of formula (IXb).

Compounds of the formula (IXb) can be converted by compounds of the formula (IXa) by removal of the protecting group. The protecting group can be remove by treatment under suitable conditions such as 1) with acid, such as hydrogen chloride, trifluoroacetic acid, and the like in organic solvent such as 1,4-dioxane, dichloromethane, and the like, or 2) hydrogen in the presence of a catalyst such as palladium on activated carbon, platinum oxide and the like in an organic solvent such as ethyl acetate, methanol, ethanol or 3) base such as lithium hydroxide, sodium hydroxide, potassium carbonate and the like in a solvent like water, methanol, tetrahydrofuran and the like to provide compounds of the formula (IXa).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H-NMR spectra were obtained on a Varian Mercury 300-MHz NMR. Purity (%) and mass spectral data were determined with a Waters Alliance 2695 HPLC/MS (Waters Symmetry C18, 4.6×75 mm, 3.5 μm) with a 2996 diode array detector from 210-400 nm.

EXAMPLES

Example 1 provides a method for preparing representative compound of formula (I). The skilled practitioner will know how to substitute the appropriate reagents, starting materials and purification methods known to those skilled in the art, in order to prepare additional compounds of the present invention.

Example 1

2-Amino-N-(6-trifluoromethoxy-benzothiazol-2-yl)-acetamide, Cpd 1

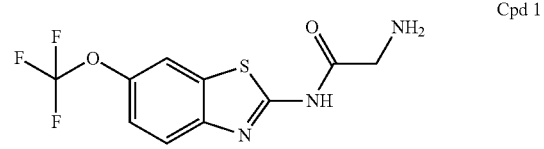 [SMILES: NCC(=O)Nc1nc2ccc(OC(F)(F)F)cc2s1]

Cpd 1

6-Trifluoromethoxy-benzothiazol-2-ylamine (100 mg, 0.42 mmol), tert-butoxycarbonylamino-acetic acid (75 mg, 0.43 mmol), and EDCI (123 mg, 0.65 mmol) were combined in methylene chloride (5 mL) and stirred 24 h at ambient temperature. The reaction was washed with 0.1N HCl (2×10 mL), dried over magnesium sulfate, filtered, and then concentrated. Chromatography on silica gel using 20% ethyl acetate: hexanes as eluent and then concentration afforded an oil. The oil was dissolved in 4N HCl and 1,4-dioxane and stirred 3 h. The reaction was concentrated to afford 2-Amino-N-(6-trifluoromethoxy-benzothiazol-2-yl)-acetamide, Cpd 1. $^1$H NMR (300 MHz, DMSO) δ 8.43 (s, 1H), 8.17 (s, 1H), 7.89 (t, J=10.4 Hz, 1H), 7.56-6.99 (m, 2H), 3.98 (m, 2H). MS m/z (M$^+$) 291.9.

Following the procedure described above for Example 1 and substituting the appropriate reagents, starting materials, and purification methods known to those skilled in the art, the following compounds of the present invention (table 9) were prepared:

TABLE 9

| Cpd | Cpd Name and Characterization Data |
|---|---|
| 2 | (R)-2-Amino-N-(6-trifluoromethoxy-benzothiazol-2-yl)-propionamide<br>$^1$H NMR (300 MHz, DMSO) δ 8.57 (s, 1H), 8.18 (s, 1H), 7.88 (d, J = 8.8 Hz, 1H), 7.46 (d, J = 8.8 Hz, 1H), 3.98 (bs, 3H), 1.46 (d, J = 7.1 Hz, 3H).<br>MS m/z (M$^+$) 305.9 |
| 4 | (R)-2-Amino-3-phenyl-N-(6-trifluoromethoxy-benzothiazol-2-yl)-propionamide<br>$^1$H NMR (300 MHz, DMSO) δ 8.75 (bs, 2H), 8.31 (s, 1H), 7.99 (d, J = 8.9 Hz, 1H), 7.59 (d, J = 8.8 Hz, 1H), 7.42 (m, 4H), 4.53 (bs, 1H), 3.44 (s, 2H), 3.32 (m, 2H).<br>MS m/z(M$^+$) 381.9 |
| 5 | (R)-2-Amino-3-benzyloxy-N-(6-trifluoromethoxy-benzothiazol-2-yl)-propionamide<br>$^1$H NMR (300 MHz, DMSO) δ 8.37 (d, J = 103.5 Hz, 1H), 8.20 (s, 1H), 7.89 (d, J = 8.8 Hz, 1H), 7.48 (d, J = 9.6 Hz, 1H), 7.40-7.18 (m, 5H), 4.57 (q, J = 12.4 Hz, 2H), 4.42 (m, 2H), 4.06-3.82 (m, 1H), 3.50 (s, 1H).<br>MS m/z (M$^+$) 411.9 |
| 7 | (S)-2-Amino-N-(6-trifluoromethoxy-benzothiazol-2-yl)-propionamide<br>$^1$H NMR (300 MHz, DMSO) δ 8.57 (s, 1H), 8.18 (s, 1H), 7.88 (d, J = 8.8 Hz, 1H), 7.46 (d, J = 8.8 Hz, 1H), 4.78-3.63 (m, 1H), 1.46 (d, J = 7.1Hz, 3H).<br>MS m/z (M$^+$) 305.9 |
| 11 | (S)-2-Amino-3-methyl-N-(6-trifluoromethoxy-benzothiazol-2-yl)-butyramide<br>$^1$H NMR (300 MHz, DMSO) δ 8.55 (s, 1H), 8.18 (s, 1H), 7.88 (d, J = 8.8 Hz, 1H), 7.46 (d, J = 8.9 Hz, 1H), 4.00 (m, 1H), 3.43 (m, 2H), 3.16 (s, 4H), 2.26 (d, J = 6.4 Hz, 1H), 1.29-0.63 (m, 6H).<br>MS m/z (M$^+$) 333.9 |
| 9 | (S)-2-Amino-3-phenyl-N-(6-trifluoromethoxy-benzothiazol-2-yl)-propionamide<br>$^1$H NMR (300 MHz, CD$_3$OD) δ 7.90 (s, 1H), 8.05-7.47 (m, 2H), 7.81 (d, J = 8.9 Hz, 1H), 7.34 (dt, J = 9.7, 7.8 Hz, 2H), 7.34 (dt, J = 9.7, 7.8 Hz, 2H), 4.40 (dd, J = 8.1, 6.3 Hz, 1H), 3.46-3.30 (m, 2H), 3.19 (dd, J = 14.0, 8.2 Hz, 1H).<br>MS m/z (M$^+$) 381.9 |
| 10 | (S)-2-Amino-3-benzyloxy-N-(6-trifluoromethoxy-benzothiazol-2-yl)-propionamide $^1$H NMR (300 MHz, DMSO) δ 8.66 (s, 1H), 8.19 (s, 1H), 7.88 (d, J = 8.9 Hz, 1H), 7.47 (d, J = 8.9 Hz, 1H), 7.35-7.18 (m, 5H), 4.56 (q, J = 12.3 Hz, 2H), 4.44 (s, 2H), 4.11-3.77 (m, 2H).<br>MS m/z (M$^+$) 411.9<br>(S)-2-amino-3-(4-fluorobenzyloxy)-N-(6-trifluoromethoxy-benzothiazol-2-yl)-propanamide: $^1$H NMR (300 MHz, DMSO) δ 8.19 (d, J = 1.4 Hz, 1H), 7.88 (d, J = 8.8 Hz, 1H), 7.47 (ddd, J = 8.8, 2.5, 0.9 Hz, 1H), 7.40-7.26 (m, 2H), 7.14-7.01 (m, 2H), 4.66-4.34 (m, 3H), 4.06-3.77 (m, 2H).: MS m/z (M+) 429.9 |

TABLE 9-continued

Cpd | Cpd Name and Characterization Data
---|---

(S)-2-amino-3-(2,4-difluorobenzyloxy)-N-(6-trifluoromethoxy-benzothiazol-2-yl)-propanamide: $^1$H NMR (300 MHz, DMSO) δ 8.19 (d, J = 1.3 Hz, 1H), 7.88 (d, J = 8.9 Hz, 1H), 7.62-7.36 (m, 2H), 7.23-7.12 (m, 1H), 7.02 (ddd, J = 9.4, 8.0, 2.5 Hz, 1H), 4.59 (q, J = 12.3 Hz, 2H), 4.44 (t, J = 4.3 Hz, 1H), 4.11-3.83 (m, 2H). MS m/z (M+) 447.9

(S)-2-amino-3-methoxy-N-(6-trifluoromethoxy-benzothiazol-2-yl)-propanamide: $^1$H NMR (300 MHz, DMSO) δ 8.65 (bs, 2H), 8.18 (d, J = 1.5 Hz, 1H), 7.87 (d, J = 8.8 Hz, 1H), 7.46 (ddd, J = 8.8, 2.5, 0.9 Hz, 1H), 4.42 (bs, 1H), 3.92 (dd, J = 10.8, 5.1 Hz, 1H), 3.82 (dd, J = 10.8, 3.8 Hz, 1H), 3.31 (s, 3H). MS m/z (M+) 335.9

(S)-N-(6-trifluoromethoxy-benzthiazol-2-yl)-pyrrolidine-2-carboxamide: $^1$H NMR (300 MHz, DMSO) δ 8.19-8.17 (m, 1H), 7.88 (d, J = 8.8 Hz, 1H), 7.53-7.22 (m, 1H), 4.56 (dd, J = 8.5, 6.7 Hz, 1H), 3.41-3.13 (m, 2H), 2.48-2.34 (m, 1H), 2.10-1.75 (m, 3H). MS m/z (M+) 331.9

(S)-tert-butyl3-(benzyloxy)-1-oxo-1-(6-trifluoromethoxy-benzothiazol-2-ylamino)-propan-2-ylcarbamate: $^1$H NMR (300 MHz, CDCl$_3$) δ 7.78 (d, J = 8.8 Hz, 1H), 7.69 (d, J = 1.2 Hz, 1H), 7.38-7.27 (m, 6H), 5.43 (d, J = 7.3 Hz, 1H), 4.59 (q, J = 11.9 Hz, 2H), 4.05 (d, J = 9.7 Hz, 1H), 3.69 (dd, J = 9.4, 5.6 Hz, 1H), 1.36 (s, 9H). MS m/z (M+) 512.0

(S)-2-acetamido-3-(benzyloxy)-N-(6-trifluoromethoxy-benzothiazol-2-yl)-propanamide: $^1$H NMR (300 MHz, CDCl$_3$) δ 7.80 (d, J = 8.9 Hz, 1H), 7.69 (s, 1H), 7.47-7.25 (m, 6H), 5.04 (t, J = 6.5 Hz, 1H), 4.63 (dd, J = 33.0, 12.1 Hz, 2H), 4.39 (dd, J = 10.0, 6.3 Hz, 1H), 3.82 (dd, J = 9.8, 7.1 Hz, 1H), 2.48 (s, 3H). MS m/z (M+) 453.9

(S)-3-tert-butoxy-2-amino-N-(6-(trifluoromethoxy)benzo[d]thiazol-2-yl)propanamide: $^1$H NMR (300 MHz, CDCl$_3$) δ 7.77 (d, J = 9.2 Hz, 1H), 7.68 (m, 1H), 7.30 (dm, J = 9.2 Hz, 1H), 3.62-3.78 (m, 3H), 1.21 (s, 9H). MS m/z (M$^+$) 321.95

Example 2

(6-Trifluoromethoxy-benzothiazol-2-yl)-carbamic acid methyl ester, Cpd 12

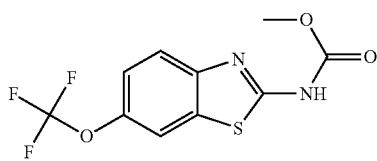

Cpd 12

6-Trifluoromethoxy-benzothiazol-2-ylamine (100 mg, 0.42 mmol), methylchloroformate (70 mg, 0.74 mmol), and triethylamine (64 mg, 0.64 mmol) were combined in methylene chloride (3 mL) and stirred 24 h at ambient temperature. The reaction was concentrated. The residue was treated with methanol/water (1:1, 5 mL) and the solid collected by filtration and dried under vacuum to afford (6-Trifluoromethoxy-benzothiazol-2-yl)-carbamic acid methyl ester, Cpd 12. $^1$H NMR (300 MHz, DMSO) δ 8.22 (s, 1H), 7.89 (d, J=8.8 Hz, 1H), 7.52 (d, J=9.0 Hz, 1H), 3.97 (s, 1H), 3.44 (s, 3H). MS m/z (M$^+$) 292.9

Following the procedure described above for Example 2 and substituting the appropriate reagents, starting materials, and purification methods known to those skilled in the art, the compounds of the present invention in table 10 were prepared:

TABLE 10

13 (6-Trifluoromethoxy-benzothiazol-2-yl)-carbamic acid ethyl ester
$^1$H NMR (300 MHz, DMSO) δ 8.23 (s, 1H), 7.90 (d, J = 8.8 Hz, 1H), 7.52 (d, J = 8.7 Hz, 1H), 4.40 (q, J = 7.1 Hz, 2H), 1.42 (t, J = 7.1 Hz, 3H). MS m/z (M$^+$) 306.9

14 (6-Trifluoromethoxy-benzothiazol-2-yl)-carbamic acid propyl ester
$^1$H NMR (300 MHz, DMSO) δ 12.15 (s, 1H), 8.10 (s, 1H), 7.77 (d, J = 8.8 Hz, 1H), 7.39 (d, J = 8.6 Hz, 1H), 4.18 (t, J = 6.7 Hz, 2H), 2.57-2.45 (m, 2H), 0.95 (t, J = 7.4 Hz, 3H). MS m/z (M$^+$) 320.9

15 (6-Trifluoromethoxy-benzothiazol-2-yl)-carbamic acid butyl ester
$^1$H NMR (300 MHz, DMSO) δ 12.14 (s, 1H), 8.09 (s, 1H), 7.77 (d, J = 8.8 Hz, 1H), 7.39 (d, J = 7.4 Hz, 1H), 4.21 (t, J = 6.7 Hz, 1H), 1.73-1.31 (m, 2H), 1.32 (t, J = 6.9 Hz, 2H), 0.88 (t, J = 6.7 Hz, 3H). MS m/z (M$^+$) 334.9

16 (6-Trifluoromethoxy-benzothiazol-2-yl)-carbamic acid isobutyl ester
$^1$H NMR (300 MHz, DMSO) δ 12.16 (s, 1H), 8.08 (s, 1H), 7.76 (d, J = 8.8 Hz, 1H), 7.38 (d, J = 7.2 Hz, 1H), 3.97 (dd, J = 18.1, 6.6 Hz, 2H), 1.96 (dt, J = 13.5, 6.8 Hz, 1H), 1.05 (d, J = 6.6 Hz, 3H). MS m/z (M$^+$) 334.9

17 (6-Trifluoromethoxy-benzothiazol-2-yl)-carbamic acid hexyl ester
$^1$H NMR (300 MHz, DMSO) δ 8.12 (s, 1H), 7.79 (d, J = 8.8 Hz, 1H), 7.42 (d, J = 7.4 Hz, 1H), 4.24 (t, J = 6.7 Hz, 2H), 1.67 (dd, J = 14.2, 6.8 Hz, 2H), 1.35 (m, 6H), 0.91 (t, J = 6.7 Hz, 3H). MS m/z (M$^+$) 362.9

18 (6-Trifluoromethoxy-benzothiazol-2-yl)-carbamic acid 2-dimethylamino-ethyl ester $^1$H NMR (300 MHz, CD$_3$OD) δ 7.85 (s, 1H), 7.75 (d, J = 9.1 Hz, 1H), 7.42-7.27 (m, 1H), 4.86 (s, 6H), 4.64 (m, 2H), 3.58 (m, 2H). MS m/z (M$^+$) 349.8

TABLE 10-continued 19 (6-Trifluoromethoxy-benzothiazol-2-yl)-carbamic acid 3-dimethylamino-propyl ester $^1$H NMR (300 MHz, DMSO) δ 10.33 (s, 1H), 8.10 (s, 1H), 7.77 (d, J =8.8 Hz, 1H), 7.39 (d, J = 8.7 Hz, 1H), 4.26 (dd, J = 18.9, 12.6 Hz, 2H), 3.16 (d, J = 15.6 Hz, 2H), 2.76 (d, J = 5.0 Hz, 6H), 2.30-1.77 (m, 2H). MS m/z (M$^+$) 363.9

Example 3

N-(6-Trifluoromethoxy-benzothiazol-2-yl)-succinamic acid, Cpd 20

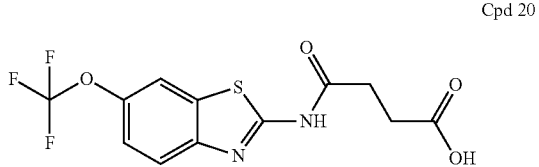 [SMILES: O=C(O)CCC(=O)Nc1nc2ccc(OC(F)(F)F)cc2s1]

6-Trifluoromethoxy-benzothiazol-2-ylamine (50 mg, 0.21 mmol), succinic anhydride (21 mg, 0.21 mmol), and triethylamine (42 mg, 0.42 mmol) were combined in tetrahydrofuran and dimethylformamide (1 mL of each) and stirred 24 h at ambient temperature. The reaction was purified using reverse phase chromatography (10-90% acetonitrile:water both containing 0.1% trifluoroacetic acid). The fractions containing product were combined and lyophilized to afford N-(6-Trifluoromethoxy-benzothiazol-2-yl)-succinamic acid, Cpd 20. $^1$H NMR (300 MHz, DMSO) δ 8.11 (s, 1H), 7.81 (d, J=8.8 Hz, 1H), 7.41 (d, J=8.8 Hz, 1H), 2.72 (d, J=6.8 Hz, 2H), 2.68-2.44 (m, 2H). MS m/z (M$^+$) 334.8

Following the procedure described above for Example 1 and Example 3 and substituting the appropriate reagents, starting materials, and purification methods known to those skilled in the art, the compounds of the present invention in table 11 were prepared:

TABLE 11

21 N-(6-Trifluoromethoxy-benzothiazol-2-yl)-succinamic acid methyl ester
$^1$H NMR (300 MHz, DMSO) δ 12.54 (s, 2H), 8.12 (s, 1H), 7.82 (d, J = 8.8 Hz, 1H), 7.42 (d, J = 8.8 Hz, 1H), 3.60 (d, J = 9.2 Hz, 3H), 3.03-2.58 (m, 2H), 1.76 (t, J = 6.6 Hz, 2H). MS m/z (M$^+$) 348.9

22 N-(6-Trifluoromethoxy-benzothiazol-2-yl)-succinamic acid tert-butyl ester
$^1$H NMR (300 MHz, DMSO) δ 12.50 (s, 1H), 8.10 (s, 1H), 7.81 (d, J = 8.6 Hz, 1H), 7.40 (m, 1H), 3.59 (t, J = 6.6 Hz, 2H), 1.75 (t, J = 6.6 Hz, 2H), 1.37 (s, 9H). MS m/z (MH$^+$—C$_4$H$_9$) 334.8

23 N-Pyridin-3-ylmethyl-N'-(6-trifluoromethoxy-benzothiazol-2-yl)-succinamide
$^1$H NMR (300 MHz, DMSO) δ 12.50 (s, 1H), 8.84-8.42 (m, 2H), 8.10 (d, J = 7.4 Hz, 2H), 7.81 (d, J = 8.8 Hz, 2H), 7.71 (d, J = 7.9 Hz, 1H), 7.35 (dd, J = 36.7, 27.4 Hz, 1H), 4.40 (d, J = 5.8 Hz, 2H), 2.78 (t, J = 6.7 Hz, 2H), 2.57 (t, J = 6.7 Hz, 2H). MS m/z (M$^+$) 424.9

24 N-(2-Morpholin-4-yl-ethyl)-N'-(6-trifluoromethoxy-benzothiazol-2-yl)-succinamide $^1$H NMR (300 MHz, DMSO) δ 12.51 (s, 1H), 9.61 (s, 1H), 8.23 (s, 1H), 8.11 (s, 1H), 7.82 (d, J = 8.9 Hz, 1H), 7.42 (d, J = 8.9 Hz, 1H), 3.96 (s, 2H), 3.64 (s, 3H), 3.44 (m, 6H), 3.18 (m, 3H), 2.76 (d, J = 6.4 Hz, 2H), 2.53 (dd, J = 15.1, 4.8 Hz, 1H). MS m/z (M$^+$) 446.9

Following the procedure described above for Example 1 and substituting the appropriate reagents, starting materials, and purification methods known to those skilled in the art, the compounds of the present invention in table 12 were prepared:

TABLE 12

25 5-Methylamino-pentanoic acid (6-trifluoromethoxy-benzothiazol-2-yl)-amide
$^1$H NMR (300 MHz, CD$_3$OD) δ 7.8 (m, 1H), 7.38 (d, J = 8.9 Hz, 1H), 3.76 (t, J = 6.6 Hz, 2H), 3.18 (m, 2H), 2.63 (t, J = 7.0 Hz, 2H), 2.11 (m, 2H), 1.83 (m, 2H). MS m/z (M$^+$) 333.9

26 5-Amino-pentanoic acid (6-trifluoromethoxy-benzothiazol-2-yl)-amide
$^1$H NMR (300 MHz, CD$_3$OD) δ 8.00-7.65 (m, 2H), 7.34 (d, J = 8.9 Hz, 1H), 3.72 (t, J = 6.6 Hz, 2H), 3.20-2.89 (m, 2H), 2.71 (t, J = 7.0 Hz, 2H), 2.17-1.93 (m, 2H), 1.93-1.73 (m, 2H). MS m/z (M+Na$^+$) 342.0

27 2-(2-Nitro-phenyl)-N-(6-trifluoromethoxy-benzothiazol-2-yl)-acetamide
$^1$H NMR (300 MHz, DMSO) δ 12.79 (s, 1H), 8.12 (d, J = 8.2 Hz, 2H), 7.84 (d, J = 8.8 Hz, 1H), 7.75 (d, J = 7.4 Hz, 1H), 7.62 (d, J = 5.6 Hz, 2H), 7.42 (d, J = 8.7 Hz, 1H), 4.30 (s, 2H). MS m/z (M$^+$) 397.9

28 4-Amino-N-(6-trifluoromethoxy-benzothiazol-2-yl)-benzamide $^1$H NMR (300 MHz, DMSO) δ 8.10 (s, 1H), 7.92 (d, J = 8.3 Hz, 1H), 7.81 (d, J = 8.8 Hz, 1H), 7.66 (s, 1H), 7.42 (d, J = 9.1 Hz, 1H), 6.69 (s, 2H). MS m/z (M$^+$) 353.9

29 2-(1-Aminomethyl-cyclohexyl)-N-(6-trifluoromethoxy-benzothiazol-2-yl)-acetamide $^1$H NMR (300 MHz, DMSO) δ 12.70 (s, 1H), 8.88 (s, 1H), 8.14 (s, 1H), 7.97 (s, 1H), 7.85 (d, J = 8.8 Hz, 1H), 7.44 (d, J = 8.8 Hz, 1H), 3.01 (d, J = 5.6 Hz, 4H), 2.90 (s, 3H), 2.80 (s, 3H), 2.74 (s, 3H), 1.47 (d, J = 8.8 Hz, 3H). MS m/z (MH$^+$) 388.0

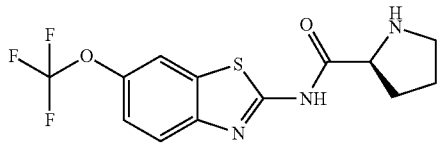 [SMILES: O=C(Nc1nc2ccc(OC(F)(F)F)cc2s1)[C@@H]1CCCN1]

Example 4

Synthesis of (S)—N-(6-(trifluoromethoxy)benzo[d]thiazol-2-yl)pyrrolidine-2-carboxamide. To a mixture of Riluzole (0.6 gm, 2.4 mmol), (S)-Boc proline (0.77 gm, 3.6 mmol) was added 1-ethyl-3-(3-dimethylaminopropyl)carbodiimide) (0.7 gm, 3.6 mmol), diisopropylethylamine (0.47 gm, 3.6 mmol) and 4-Dimethylaminopyridine (0.06 gm, 0.5 mmol) in anhydrous N, N-dimethylformamide (8 mL) and stirred for 20 hours. The reaction mixture was quenched with water (5 mL) diluted with ethyl acetate (50 mL) and the aqueous layer was extracted with ethyl acetate (2×5 mL). The combined organic layers were washed with 1N HCl (10 mL), saturated NaHCO$_3$ (10 mL), water (2×20 mL) and brine (10 mL). The organic layer was then filtered through Na$_2$SO$_4$ concentrated under reduced pressure and purified via flash column chromatography using 20-30% ethyl acetate that afforded a white solid. This was dissolved in 1:1 4N HCl in 1,4-dioxane: 1,4-dioxane and stirred for 3 hours. After 3 hours the solvent was removed under reduced pressure and the resulting solid was washed with ethyl acetate (5 mL) and ether (5 mL). The solid was then filtered and dried to afford (S)—N-(6-(trifluoromethoxy)benzo[d]thiazol-2-yl)pyrrolidine-2-carboxamide (60%). $^1$H NMR (300 MHz, DMSO) δ 8.19-8.17 (m, 1H), 7.88 (d, J=8.8 Hz, 1H), 7.53-7.22 (m, 1H), 4.56 (dd, J=8.5, 6.7 Hz, 1H), 3.41-3.13 (m, 2H), 2.48-2.34 (m, 1H), 2.10-1.75 (m, 3H). MS m/z (M+) 331.9.

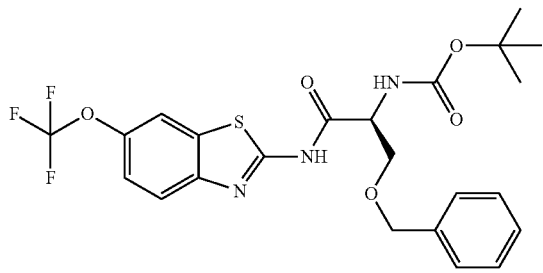 [SMILES: CC(C)(C)OC(=O)N[C@@H](COCc1ccccc1)C(=O)Nc1nc2ccc(OC(F)(F)F)cc2s1]

Synthesis of tert-butyl-N—[(S)-2-(benzyloxy)-1-{[6-(trifluoromethoxy)-1,3-benzothiazol-2-yl]carbamoyl}ethyl]carbamate. To a solution of 6-(trifluoromethoxy)-1,3-benzothiazol-2-amine (Riluzole, 5.0 g, 21 mmol), (S)—N-t-butyloxycarbonyl-serine-O-benzyl ether (7.6 g, 26 mmol), hydroxybenzotriazole (4.0 g, 26 mmol), 4-dimethylaminopyridine (0.32 g, 2.6 mmol) and diisopropylethylamine (3.4 g, 26 mmol, 4.7 mL) in N, N-dimethylformamide (100 mL) was added 1-ethyl-3-(3-dimethylaminopropyl)carbodiimide) (5.0 g, 26 mmol) and the mixture stirred for 24 hours. The reaction mixture was diluted with ethyl acetate (500 mL) and washed with water (2×300 mL), 1N HCl (6×200 mL), water (300 mL), 1M sodium carbonate (200 mL), brine (100 mL), dried (Na$_2$SO$_4$) and evaporated to a colorless viscous oil (5.0 g, 47%). $^1$H-NMR (300 MHz, CDCl$_3$) δ 7.77 (d, J=9.1 Hz, 1H), 7.69 (d, J=1.1 Hz, 1H), 7.30 (m, 6H), 5.45 (d, J=7.3 Hz, 1H), 4.61 (d ABq, J=12.0 Hz, 1H), 4.56 (d ABq, J=12.0 Hz, 1H), 4.03 (m, 1H), 3.69 (dd, J=9.6 Hz, J=5.5 Hz, 1H), 1.47 (s, 9H); ESI MS (M+H)$^+$=512.

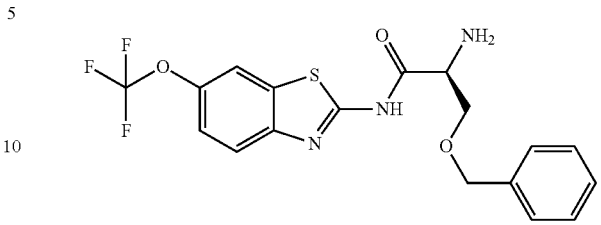

Synthesis of (S)-2-amino-3-(benzyloxy)-N-[6-(trifluoromethoxy)-1,3-benzothiazol-2-yl]propanamide. A solution of tert-butyl N—[(S)-2-(benzyloxy)-1-{[6-(trifluoromethoxy)-1,3-benzothiazol-2-yl]carbamoyl}ethyl]carbamate (5.0 g, 9.8 mmol) in dichloromethane (30 mL) and trifluoroacetic acid (15 mL) was stirred for 1 hour then evaporated to dryness. The residue was dissolved in ethyl acetate (100 mL) and washed with saturated sodium bicarbonate solution (100 mL), water (100 mL) and brine (50 mL). The mixture was dried (Na$_2$SO$_4$) and evaporated to a gum that was dissolved in acetonitrile (150 mL) and treated with concentrated HCl (1.2 mL). The hydrochloride salt precipitated and was filtered, washed with ethyl acetate and dried to leave 3.0 g (68%) of off-white powder. $^1$H-NMR (300 MHz, DMSO-d$_6$) δ 8.16 (dd, J=1.5 Hz, J=1.0 Hz, 1H), 7.86 (d, J=8.8 Hz, 1H), 7.45 (ddd, J=8.8 Hz, J=1.0 Hz, J=1.5 Hz, 1H), 7.25 (m, 5H), 4.54 (ABq, J=12.3 Hz, 2H), 4.41 (dd, J=4.1 Hz, J=4.4 Hz, 1H), 3.93 (m, 2H); ESI MS (M+H)$^+$=412.

Formulations

The present invention also relates to compositions or formulations which comprise the riluzole pro-drug agents according to the present invention. In general, the compositions of the present invention comprise an effective amount of one or more riluzole pro-drug agents and salts thereof according to the present invention which are effective and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known riluzole pro-drug agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more riluzole pro-drug according to the present invention and one or more excipients; from about 0.01 mg to about 100 mg of one or more riluzole pro-drug according to the present invention and one or more excipients; and from about 0.1 mg to about 10 mg of one or more riluzole pro-drug according to the present invention; and one or more excipients.

Procedures

The following procedures can be utilized in evaluating and selecting compounds as riluzole pro-drugs.

Stability in Simulated Gastric Fluid (SGF) and Simulated Intestinal Fluid (SIF). Procedure from Baudy et. al. (J. Med. Chem. 2009, 52, 771-778) used. The physiological stability of pro-drugs was determined by examining the stability of the compound in SGF, and SIF at 37° C. The compounds were prepared in a 9:1 mixture of the appropriate test component (SGF, SIF) and acetonitrile to a final concentration of 0.01 mg/mL. The samples were thoroughly mixed and maintained at 37° C. Each sample was injected consecutively onto an Agilent 1100 system (Luna C18, 3 µm, 50 mm×3 mm; 1 mL/min; mobile phase of 0.1% trifluoroacetic acid in water/0.1% trifluoroacetic acid in acetonitrile) after a 3 h period. The percent remaining of pro-drug was calculated by comparing the area of pro-drug compound versus riluzole generated. The identities of the parent compounds and conversion products were confirmed by LC/MS.

Plasma Stability: Assessment of plasma stability was carried out by individual incubations of drug candidates in fresh mouse or human control plasma at a concentration of 1 uM for 1 hour at 37° C. After which, the samples were de-proteinized by addition of 2 volumes of acetonitrile containing 0.1% formic acid and internal standard, vortex mixed for 2 minutes and centrifuged at 4000 rpm for 10 minutes to pellet precipitated protein. The resulting supernatant containing the drug candidates was diluted 5-fold with water containing 0.1% formic acid and submitted to LC-MS/MS analysis. All determinations were done in triplicate. Plasma stability was expressed as percent of control remaining.

Metabolic Stability: In vitro metabolic stability was determined in pooled mouse or human liver microsomes (BD Gentest) at a protein concentration of 0.5 mg/mL in reaction buffer (100 mM $KH_2PO_4$, pH 7.4 and 12 mM $MgCl_2$). Each drug candidate was added to a final concentration of 1 uM. This mixture was pre-warmed to 37° C. for 10 minutes prior to starting the reaction with the addition of β-Nicotinamide adenine dinucleotide 2'-phosphate reduced (NADPH) to a final concentration of 1 mM. A parallel incubation lacking NADPH served as the control. After incubation for 30 min at 37° C., the reactions were quenched by the addition of acetonitrile containing 0.1% formic acid and internal standard, vortex mixed for 2 minutes and centrifuged at 4000 rpm for 10 minutes to pellet the precipitated protein. The resulting supernatant containing the drug candidate and its potential metabolites was diluted 5-fold with water containing 0.1% formic acid and submitted to LC-MS/MS analysis. Metabolic stability was expressed as percent of control remaining.

LC-MS/MS Analysis: An aliquot from each incubation was analyzed by LC-MS/MS with SRM detection in the positive ionization mode using an ABSciex API 5500 QTrap Mass Spectrometer interfaced via the ABSciex Turbo V IonSpray source (ESI) to an Eksigent ExpressHT LC system. Best peak shape and separation from interfering matrix species was afforded by an Eksigent 3C18-CL-300, 3μ, 50×1 mm column. A fast gradient, from 15 to 85% organic in 2.5 minutes, with run time of 5.0 minutes, and flow rate of 50 uL/min was utilized. Peak areas were integrated using MultiQuant v2.0 software from ABSciex.

TABLE 13

Values represent percent of pro-drug metabolized to riluzole.

| Cpd # | SGF (3 hours) | SIF (3 hours) | Metabolic Stability mouse (30 minutes) | Metabolic Stability human (30 minutes) | Plasma Stability mouse (1 hour) | Plasma Stability Human (1 hour) |
|---|---|---|---|---|---|---|
| 1 |  |  | 4 | 7 | 11 | 3 |
| 2 | 0 | 50 | 10 | 4 | 36 | 15 |
| 4 | 3 | 0 | 12 | 18 | 47 | 6 |
| 5 |  |  | 24 | 0 | 25 | 3 |
| 7 | 0 | 50 | 1 | 0 | 28 | 10 |
| 9 |  |  | 2 | 0 | 0 | 7 |
| 10 | 0 | 0 | 0 | 15 | 52 | 9 |
| 11 | 0 | 40 | 40 | 6 | 45 | 11 |
| 12 | 0 | 0 | 10 | 0 | 0 | 15 |
| 13 | 0 | 0 | 8 | 7 | 0 | 0 |
| 14 | 0 | 0 | 15 | 34 | 0 | 0 |
| 15 | 0 | 0 | 53 | 13 | 9 | 0 |
| 16 | 5 | 0 | 23 | 14 | 0 | 0 |
| 17 | 0 |  |  |  |  |  |
| 18 | 0 | 0 | 13 | 10 | 3 | 0 |
| 19 | 0 | 0 | 71 | 0 | 0 | 0 |
| 20 | 0 | 0 | 70 | 0 | 0 | 16 |
| 21 | 3 | 0 | 77 | 34 | 99 | 25 |
| 22 | 0 | 0 | 0 | 21 | 0 | 0 |
| 23 | 0 | 10 | 0 | 4 | 26 | 0 |
| 24 | 0 | 60 |  |  |  |  |
| 25 | 0 | 0 | 78 | 0 | 0 | 0 |
| 26 | 0 | 0 | 66 | 19 | 0 | 5 |
| 27 | 0 | 0 | 59 | 22 | 0 | 13 |
| 28 | 0 | 0 | 24 | 80 | 0 | 0 |
| 29 | 0 | 50 |  |  |  |  |

What is claimed is:

1. A method for treating a non-proliferative disease in which riluzole is clinically relevant, said method comprising administering to a subject an effective amount of at least one compound of the formula (III):

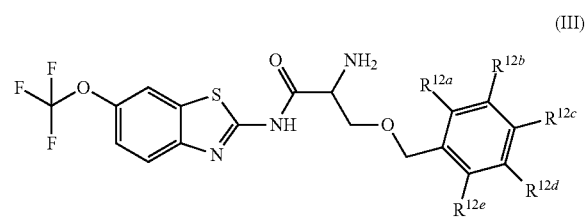

(III)

including hydrates, solvates, pharmaceutically acceptable salts, and complexes thereof, wherein $R^{12a}$, $R^{12b}$, $R^{12c}$, $R^{2d}$, and $R^{12e}$ are each independently selected from the group consisting of hydrogen, deuterium, halogen, trifluoromethyl, triflouromethoxy, optionally substituted C1-C6 alkyl, and optionally substituted C1-C6 alkoxy; wherein the disease in which riluzole is clinically relevant is amyotrophic lateral sclerosis, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, or Huntington's disease.

2. A method for treating a non-proliferative disease in which riluzole is clinically relevant, said method comprising administering to a subject an effective amount of at least one at least one compound of:

2-Amino-N-(6-trifluoromethoxy-benzothiazol-2-yl)-acetamide;
(R)-2-Amino-N-(6-trifluoromethoxy-benzothiazol-2-yl)-propionamide;
(R)-2-Amino-3-phenyl-N-(6-trifluoromethoxy-benzothiazol-2-yl)-propionamide;
(R)-2-Amino-3-benzyloxy-N-(6-trifluoromethoxy-benzothiazol-2-yl)-propionamide;
(S)-2-Amino-N-(6-trifluoromethoxy-benzothiazol-2-yl)-propionamide;
(S)-2-Amino-3-methyl-N-(6-trifluoromethoxy-benzothiazol-2-yl)-butyramide;
(S)-2-Amino-3-phenyl-N-(6-trifluoromethoxy-benzothiazol-2-yl)-propionamide;
(S)-2-Amino-3-benzyloxy-N-(6-trifluoromethoxy-benzothiazol-2-yl)-propionamide;
(S)-2-amino-3-(4-fluorobenzyloxy)-N-(6-trifluoromethoxy-benzothiazol-2-yl)-propanamide;
(S)-2-amino-3-(2,4-difluorobenzyloxy)-N-(6-trifluoromethoxy-benzothiazol-2-yl)-propanamide;
(S)-2-amino-3-methoxy-N-(6-trifluoromethoxy-benzothiazol-2-yl)-propanamide;
(S)-3-tert-butoxy-2-amino-N-(6-(trifluoromethoxy)benzo[d]thiazol-2-yl)propanamide;
(6-Trifluoromethoxy-benzothiazol-2-yl)-carbamic acid methyl ester;
(6-Trifluoromethoxy-benzothiazol-2-yl)-carbamic acid ethyl ester;
(6-Trifluoromethoxy-benzothiazol-2-yl)-carbamic acid propyl ester;
(6-Trifluoromethoxy-benzothiazol-2-yl)-carbamic acid butyl ester;
(6-Trifluoromethoxy-benzothiazol-2-yl)-carbamic acid isobutyl ester;
(6-Trifluoromethoxy-benzothiazol-2-yl)-carbamic acid hexyl ester;
(6-Trifluoromethoxy-benzothiazol-2-yl)-carbamic acid 2-dimethylamino-ethyl ester;
(6-Trifluoromethoxy-benzothiazol-2-yl)-carbamic acid 3-dimethylamino-propyl ester;
N-(6-Trifluoromethoxy-benzothiazol-2-yl)-succinamic acid;
N-(6-Trifluoromethoxy-benzothiazol-2-yl)-succinamic acid methyl ester;
N-(6-Trifluoromethoxy-benzothiazol-2-yl)-succinamic acid tert-butyl ester;
N-Pyridin-3-ylmethyl-N'-(6-trifluoromethoxy-benzothiazol-2-yl)-succinamide;
N-(2-Morpholin-4-yl-ethyl)-N'-(6-trifluoromethoxy-benzothiazol-2-yl)-succinamide;
5-Methylamino-pentanoic acid (6-trifluoromethoxy-benzothiazol-2-yl)-amide;
5-Amino-pentanoic acid (6-trifluoromethoxy-benzothiazol-2-yl)-amide;
4-Amino-N-(6-trifluoromethoxy-benzothiazol-2-yl)-benzamide;
2-(1-Aminomethyl-cyclohexyl)-N-(6-trifluoromethoxy-benzothiazol-2-yl)-acetamide;
or a pharmaceutically acceptable form thereof;
wherein the disease in which riluzole is clinically relevant is amyotrophic lateral sclerosis, bipolar disorder, treatment resistant and major depression, obsessive-compulsive disorder, spinal muscular atrophy, radiation therapy, multiple sclerosis, chronic cerebellar ataxia, cervical spondylotic myelopathy, spinal cord injury, hereditary cerebellar ataxia, Tourette syndrome, autism spectrum disorder, schizophrenia, fragile X syndrome, Parkinson's Disease, or Huntington's disease.

3. The method of claim 1, wherein the at least one compound of the formula (III) is administered in a composition further comprising at least one excipient.

4. The method of claim 2, wherein the at least one compound is administered in a composition further comprising at least one excipient.

* * * * *